United States Patent
Kirwan

(10) Patent No.: US 12,336,910 B2
(45) Date of Patent: Jun. 24, 2025

(54) HIP PROSTHESIS

(71) Applicant: David Phillip Kirwan, Wirlinga (AU)

(72) Inventor: David Phillip Kirwan, Wirlinga (AU)

(73) Assignee: David Phillip Kirwan, Wirlinga (AU)

( * ) Notice: Subject to any disclaimer, the term of this patent is extended or adjusted under 35 U.S.C. 154(b) by 1057 days.

(21) Appl. No.: 17/338,457

(22) Filed: Jun. 3, 2021

(65) Prior Publication Data

US 2021/0290400 A1 Sep. 23, 2021

Related U.S. Application Data

(62) Division of application No. 15/765,201, filed as application No. PCT/AU2016/050922 on Sep. 29, 2016, now Pat. No. 11,045,322.

(30) Foreign Application Priority Data

Sep. 30, 2015 (AU) .................................. 2015903981

(51) Int. Cl.
*A61F 2/36* (2006.01)
*A61F 2/30* (2006.01)

(52) U.S. Cl.
CPC .......... *A61F 2/3676* (2013.01); *A61F 2/3601* (2013.01); *A61F 2/3662* (2013.01); *A61F 2002/30113* (2013.01); *A61F 2002/30125* (2013.01); *A61F 2002/3013* (2013.01); *A61F 2002/30153* (2013.01); *A61F 2002/30154* (2013.01); *A61F 2002/30593* (2013.01); *A61F 2002/30594* (2013.01); *A61F 2002/30677* (2013.01); *A61F 2002/3069* (2013.01); *A61F 2002/3686* (2013.01)

(58) Field of Classification Search
CPC ... A61F 2/3662–2002/3698; A61F 2002/4029; A61F 2/4059
See application file for complete search history.

(56) References Cited

U.S. PATENT DOCUMENTS

| 4,101,985 A | * | 7/1978 | Baumann | ................. A61F 2/34 623/22.46 |
| 4,279,042 A | * | 7/1981 | Andriacchi | ............... A61F 2/36 623/23.15 |

(Continued)

FOREIGN PATENT DOCUMENTS

| DE | 10212982 | 10/2003 |
| DE | 102007012858 | 9/2008 |

(Continued)

OTHER PUBLICATIONS

Extended European Search Report in European Appln. No. 16849960.6, dated Jul. 5, 2019, 12 pages.

(Continued)

*Primary Examiner* — Alvin J Stewart
(74) *Attorney, Agent, or Firm* — Fish & Richardson P.C.

(57) ABSTRACT

A short-stem femoral implant suitable for use in hip arthroplasty configured to self-stabilise against sliding across the endo-cortex when implanted in a subject's femur. The femoral implant includes a distal end configured to engage in abutment with the lateral endo-cortex of the subject's femur at two distal locations such that when implanted, the femoral implant has a reduced tendency for sliding across the endo-cortex.

24 Claims, 12 Drawing Sheets

(56) References Cited

U.S. PATENT DOCUMENTS

| | | | | |
|---|---|---|---|---|
| 4,435,854 A * | 3/1984 | Keller | A61F 2/3662 | 623/23.35 |
| 4,546,501 A * | 10/1985 | Gustilo | A61F 2/30907 | 606/62 |
| 4,589,883 A * | 5/1986 | Kenna | A61F 2/367 | 606/62 |
| 4,608,053 A * | 8/1986 | Keller | A61F 2/30728 | 623/23.31 |
| 4,738,681 A * | 4/1988 | Koeneman | A61F 2/36 | 623/23.35 |
| 4,813,963 A * | 3/1989 | Hori | A61F 2/3662 | 623/23.35 |
| 4,840,632 A * | 6/1989 | Kampner | A61F 2/30749 | 623/22.36 |
| 4,944,761 A * | 7/1990 | Stuhmer | A61F 2/36 | 623/23.31 |
| 4,957,510 A * | 9/1990 | Cremascoli | A61F 2/3662 | 623/22.46 |
| 5,258,033 A | 11/1993 | Lawes et al. | | |
| 5,258,035 A * | 11/1993 | Hofmann | A61F 2/3662 | 623/23.28 |
| 5,507,829 A * | 4/1996 | Thongpreda | A61F 2/30767 | 623/22.41 |
| 5,507,833 A * | 4/1996 | Bohn | A61F 2/32 | 623/23.3 |
| 5,514,184 A | 5/1996 | Doi et al. | | |
| 5,571,203 A | 11/1996 | Masini | | |
| 5,653,764 A * | 8/1997 | Murphy | A61F 2/3609 | 623/23.15 |
| 5,658,352 A * | 8/1997 | Draenert | A61F 2/36 | 623/22.4 |
| 5,888,210 A * | 3/1999 | Draenert | A61F 2/3662 | 623/23.35 |
| 6,030,417 A * | 2/2000 | Bresler | A61F 2/36 | 623/23.15 |
| 6,120,544 A * | 9/2000 | Grundei | A61F 2/3601 | 623/23.14 |
| 6,193,760 B1 * | 2/2001 | Copf | A61F 2/36 | 623/23.35 |
| 6,200,349 B1 * | 3/2001 | Naybour | A61F 2/3676 | 623/23.15 |
| 6,200,350 B1 * | 3/2001 | Masini | A61F 2/3609 | 623/23.35 |
| 6,413,280 B1 * | 7/2002 | Feiler | A61F 2/32 | 623/22.21 |
| 6,706,073 B2 * | 3/2004 | Draenert | A61F 2/36 | 623/23.26 |
| 6,723,129 B2 | 4/2004 | Dwyer et al. | | |
| 7,060,102 B2 | 6/2006 | Thompson et al. | | |
| 7,494,509 B1 * | 2/2009 | Hershberger | A61F 2/3662 | 623/22.4 |
| 7,879,106 B2 * | 2/2011 | McMinn | A61F 2/3601 | 623/22.44 |
| 7,985,261 B2 * | 7/2011 | Masini | A61F 2/36 | 623/22.21 |
| 11,045,322 B2 * | 6/2021 | Kirwan | A61F 2/3601 | |
| 2002/0045950 A1 * | 4/2002 | Draenert | A61F 2/36 | 623/23.26 |
| 2005/0055103 A1 * | 3/2005 | Badatcheff | A61F 2/30942 | 623/23.35 |
| 2006/0184250 A1 * | 8/2006 | Bandoh | A61F 2/36 | 623/23.35 |
| 2006/0190092 A1 | 8/2006 | Fridshtand et al. | | |
| 2008/0021567 A1 * | 1/2008 | Meulink | A61F 2/3609 | 623/22.12 |
| 2008/0200990 A1 * | 8/2008 | McTighe | A61F 2/36 | 623/23.35 |
| 2008/0228283 A1 * | 9/2008 | Willi | A61F 2/3609 | 623/23.35 |
| 2010/0241239 A1 | 9/2010 | Smith | | |
| 2011/0118849 A1 * | 5/2011 | Chen | A61F 2/36 | 29/428 |
| 2011/0125285 A1 * | 5/2011 | Ragbir | A61F 2/3609 | 623/23.15 |
| 2012/0259422 A1 | 10/2012 | Pappas et al. | | |
| 2013/0165938 A1 | 6/2013 | Chow et al. | | |
| 2013/0173012 A1 | 7/2013 | Schiraldi et al. | | |
| 2018/0318093 A1 | 11/2018 | Kirwan | | |
| 2021/0137688 A1 * | 5/2021 | Biggs | A61F 2/3662 | |
| 2021/0290400 A1 * | 9/2021 | Kirwan | A61F 2/3676 | |
| 2023/0009989 A1 * | 1/2023 | De Villiers | A61F 2/3662 | |

FOREIGN PATENT DOCUMENTS

| | | |
|---|---|---|
| DE | 102009017532 | 10/2010 |
| EP | 579868 | 1/1994 |
| EP | 0677281 | 10/1995 |
| EP | 1025816 | 8/2000 |
| EP | 1138283 | 10/2001 |
| EP | 2506806 | 10/2012 |
| FR | 2889444 | 10/2007 |
| GB | 1511859 | 5/1978 |
| WO | WO 1998/006359 | 2/1998 |
| WO | WO 2003/039411 | 5/2003 |
| WO | WO 2008/152478 | 12/2008 |
| WO | WO 2009/037284 | 3/2009 |
| WO | WO 2011/144915 | 11/2011 |
| WO | WO 2012/173605 | 12/2012 |

OTHER PUBLICATIONS

International Preliminary Report on Patentability in International Appln. No. PCT/AU2016/050922, dated Apr. 3, 2018.

International Search Report and Written Opinion in International Appln. No. PCT/AU2016/050922, dated Dec. 21, 2016, 19 pages.

International-Type Search Report in Australian Provisional Patent Appln. No. 2015903981, dated Mar. 3, 2016, 11 pages.

Office Action in European Appln. No. 16849960.6, dated Jul. 28, 2020, 5 pages.

Wikipedia.com [online], "Transverse Plane," Jan. 26, 2016, retrieved on Feb. 24, 2016, retrieved from, URL <https://en.wikipedia.org/wiki/Transverse_plane>, 4 pages.

\* cited by examiner

HIP PROSTHESIS

This application is a divisional patent application of U.S. National Phase Application under 35 U.S.C. § 371 of International Patent Application No. PCT/AU2016/050922, filed on Sep. 29, 2016, which claims priority from Australian Provisional Patent Application No. 2015903981 filed on Sep. 30, 2015, the contents of which are to be taken as incorporated herein by this reference.

TECHNICAL FIELD

The present invention relates to hip prostheses suitable for use in hip arthroplasty. It relates particularly but not exclusively to prostheses forming the stem of femoral implants that are configured for improved stability during impaction and/or post-operatively.

BACKGROUND OF INVENTION

Hip arthroplasty involves surgical implantation of prosthetic components to replace the bearing surfaces in a subject's damaged or diseased hip joint. The majority of subjects require these surgeries due to damage of the articular cartilage, which separates and cushions the articular surfaces of the femur and acetabulum. Cartilage may be damaged through natural degeneration with age due to osteoarthritis, or alternatively, from inflammation occurring in rheumatoid arthritis. Loss of viable cartilage causes the articular surfaces of the femur and acetabulum to bear against one another, resulting in damage to the supporting bone and pain suffered by the subject. In these circumstances, total hip arthroplasty (THA) is performed on the subject's damaged or diseased hip joint, which involves removal of the native bone and bearing surfaces and surgical implantation of a prosthesis to replace the removed bearing surfaces, thereby reducing pain and further damage to the supporting bone, as well as providing improved function.

Traditional hip prostheses used in THA typically include a femoral component and an acetabular component, which are respectively implanted into a prepared femur and a prepared acetabulum of the subject. The femoral component may include a femoral stem and a femoral head, and the acetabular component may include an acetabular cup or socket and an acetabular cup liner. While performing the THA procedure, the surgeon usually removes the damaged cartilage and prepares the femur by removing the natural femoral head and neck, and hollowing the femoral shaft to accommodate the prosthetic femoral component, within the hollowed shaft. However, loss of the femoral neck and large amounts of cancellous bone from the upper femoral shaft during preparation of the femur significantly weakens the remaining femoral bone and causes stress to be concentrated in the upper femoral shaft. This may contribute to loss of bone quality over time, due to less physiological stress being applied to the bone proximal to the level of fixation of the femoral component.

In view of the above, alternative hip prostheses have been developed with the intention to reduce the likelihood of bone and prosthesis failure. Neck-conserving or neck-preserving short-stem femoral components preserve some of the subject's femoral neck and minimise loss of bone. The femoral component is modified and shaped to retain bone of the femoral neck. The primary aim of conserving bone is to avoid or minimise stress transfer to the femoral shaft, i.e., by allowing physiological loading of bone as proximal in the femur as possible. Furthermore, the femoral component may be modified to include an elliptical cross-section and a curved and tapered shape, to obtain primary fixation during surgery and optimally distribute forces between the femoral stem and the patient's femur during physiological loading.

Despite these advances, THA involving use of short-stem hip prostheses remain susceptible to failure, most commonly due to early subsidence of the femoral stem within the femur. Subsidence may occur when the femoral stem is not securely implanted within the subject's femur, i.e., when primary stability is not obtained at the time of implantation. Micro-movement can occur after implantation, if primary stability is not obtained. Typically, short-stem hip prostheses are cementless and include a porous coating to encourage the surrounding bone of the femur to grow into the implant. Bone in-growth provides sufficient and permanent stability to prevent movement of the femoral stem during physiological loading and unloading, and therefore avoid late subsidence. However, the risk of subsidence remains during the first weeks post-operatively, if the surrounding bone does not grow into the femoral stem before loading occurs. Accordingly, loading of the femoral stem during this period may result in movement within the subject's femur. Such movement may cause abrasive destruction of the surrounding bone, so that the femoral stem loosens and subsides.

In order to prevent subsidence, neck-preserving short femoral stem prostheses have been modified to include proximal collars and proximal ribs to provide greater purchase on the femoral neck and stabilise the femoral stem during early use, i.e., before bone in-growth occurs. Conventional (neck-sacrificing) femoral stems with rhomboidal cross-sections have been commonly used, and aim to maximally fill and therefore achieve fixation within the transverse section of the subject's upper femoral shaft, and thereby reduce the likelihood of micro-movement of the femoral stem during initial stages of bone in-growth. Conventional stems, which resect the neck and have a rhomboidal cross-section, have been successful. However, neck-preserving stems that have a rhomboidal cross-section fixed to the femoral neck, which is weaker bone than the femoral shaft, have been known to fail due to intra-operative femoral fractures as well as from subsidence. Some surgeons have also attempted to encourage their patients to avoid weight-bearing in the first few weeks of recovery, to allow bone in-growth to the femoral stem. However, this strategy has not always been successful in preventing subsidence in part due to poor subject compliance.

Cementless femoral stem prostheses, once ingrown, are difficult to remove from the subject in the event of revision surgery. As outlined previously, cementless femoral stems include and rely on a porous coating to encourage in-growth of the surrounding bone for long-term fixation. However, in the event that revision surgery is required, the ingrown bone must be removed from the femoral stem. This is achieved using surgical instruments, such as chisels, in order to loosen the prosthesis for extraction from the subject. Difficulty is encountered when porous coated areas of the femoral stem are not easily accessible to the surgeon during extraction. Accordingly, the surgeon may damage the subject's femur in an effort to extract the femoral stem, which may weaken the remaining cortical bone and increase the operative complexity and extent of revision surgery, as well as the risk of failure of the revision prosthesis.

In light of the above, it is desirable to provide a short-stem femoral prosthesis suitable for preservation of and fixation in the femoral neck, and that reduces the risk of subsidence.

Further, it is desirable to provide a femoral stem that allows relative ease of removal if necessary for future revision surgery.

The discussion of the background to the invention included herein including reference to documents, acts, materials, devices, articles and the like is included to explain the context of the present invention. This is not to be taken as an admission or a suggestion that any of the material referred to was published, known or part of the common general knowledge in Australia or in any other country as at the priority date of any of the claims.

SUMMARY OF INVENTION

Viewed from one aspect of the present invention, there is provided a short-stem femoral implant suitable for use in hip arthroplasty, the femoral implant configured to self-stabilise against sliding across the endo-cortex when implanted in a subject's femur, wherein the femoral implant includes a distal end configured to engage in abutment with the lateral endo-cortex of the subject's femur at two distal locations such that when implanted, the femoral implant has a reduced tendency for sliding across the endo-cortex.

In some embodiments, the distal end includes a flat abutment structure configured to engage in abutment with the lateral endo-cortex at the two distal locations. Alternatively, the distal end may include a contoured abutment structure configured to engage in abutment with the lateral endo-cortex at the two distal locations. In other embodiments, the distal end includes two rails forming an abutment structure, wherein the two rails each include flat engagement surfaces or edges that respectively engage in abutment with the lateral endo-cortex at the two distal locations.

The two distal locations of the lateral endo-cortex may be aligned in a common transverse plane of the subject's femur although this need not be the case.

In some embodiments, the distal end is interchangeable when used with the femoral implant, for selection and use of a distal tip that is suitably shaped for the subject's anatomy.

In some embodiments, the femoral implant is further configured to self-stabilise against rotation about an elongate axis thereof when implanted in the subject's femur. The femoral implant may include a contoured surface having one or more recessed regions configured to distribute reaction forces imparted at the bone-implant interface such that when implanted, the femoral implant has a reduced tendency to rotate about the elongate axis.

Preferably, the one or more recessed regions are positioned on the femoral implant such that the reaction forces are transferred medially and/or laterally in a transverse plane of the subject's femur. The reaction forces may be transferred medially and/or laterally at successive levels along the elongate axis of the femoral implant. The one or more recessed regions may be positioned near or at a location where the femoral implant engages in abutment with the endo-cortex of the subject's femur. Preferably, the femoral implant includes two or more recessed regions on one or both of an anterior aspect and a posterior aspect of the femoral implant. The recessed regions may be formed in the contoured surface as one of: a bevel; a hollow; a flattened edge; a sloped edge; or a chamfer, and formed using manufacturing techniques known to a person skilled in the art.

In some embodiments, the femoral implant further includes a distal end or tip that is angled in a sagittal plane of the subject's femur to enable improved alignment with the subject's femoral curvature when implanted therein. The distal end or tip may be offset at an angle in a range of about 5 to 25 degrees, preferably about 10 to 20 degrees, and more preferably, approximately 15 degrees in the sagittal plane with respect to the elongate axis of the femoral implant. The distal end may be angled anteriorly in the sagittal plane with respect to the elongate axis of the femoral implant.

The femoral implant may further include a neck portion angled in a sagittal plane of the subject's femur to enable improved location of a femoral head of the implant with respect to the subject's femoral neck when implanted therein. Preferably, the neck portion is angled such that the femoral head is located posteriorly with respect to a central axis of the subject's femoral neck. The neck portion may be offset at an angle in a range of about 5 to 20 degrees, preferably about 5 to 15 degrees, and more preferably, approximately 10 degrees in the sagittal plane with respect to the elongate axis of the femoral implant. The neck portion may be angled posteriorly with respect to the elongate axis of the implant.

The femoral implant may be further configured for ease of removal from the subject's femur by including a bone in-growth coating suitably positioned for revision surgery. The coating may be positioned proximally about one-third medially and about one-half to two-thirds laterally so as to not obscure access to the femoral bone-implant interface distally during removal from the subject's femur.

In some embodiments, the femoral implant is configured to self-stabilise when implanted in the subject's femur such that micro-movement is reduced to no more than approximately 150 micrometres.

The femoral implant is configured for use as a short-stem prosthesis. The femoral implant may further be configured to preserve at least some of the subject's femoral neck when implanted therein. Thus, it may also be configured for use as a neck-preserving prosthesis.

Viewed from another aspect of the present invention, there is provided a short-stem femoral implant suitable for use in hip arthroplasty, the femoral implant configured to self-stabilise against rotation about an elongate axis thereof when implanted in a subject's femur, wherein the femoral implant includes a contoured surface having one or more recessed regions configured to distribute reaction forces imparted at the bone-implant interface such that when implanted, the femoral implant has a reduced tendency to rotate about the elongate axis.

Preferably, the one or more recessed regions are positioned on the femoral implant such that the reaction forces are transferred medially and/or laterally in a transverse plane of the subject's femur. The reaction forces may be transferred medially and/or laterally at successive levels along the elongate axis of the femoral implant. The one or more recessed regions may be positioned near or at a location where the femoral implant engages in abutment with the endo-cortex of the subject's femur. Preferably, the femoral implant includes two or more recessed regions on one or both of an anterior aspect and a posterior aspect of the femoral implant. The recessed regions may be formed in the contoured surface as one of: a bevel; a hollow; a flattened edge; a sloped edge; or a chamfer, and formed using manufacturing techniques known to a person skilled in the art.

In some embodiments, the femoral implant is further configured to self-stabilise against sliding across the endo-cortex when implanted in the subject's femur. The femoral implant may include a distal end configured to engage in abutment with the lateral endo-cortex of the subject's femur at two distal locations such that when implanted, the femoral implant has a reduced tendency for sliding across the endo-cortex.

In some embodiments, the distal end includes a flat abutment structure configured to engage in abutment with the lateral endo-cortex at the two distal locations. Alternatively, the distal end may include a contoured abutment structure configured to engage in abutment with the lateral endo-cortex at the two distal locations. In other embodiments, the distal end includes two rails forming an abutment structure, wherein the two rails each include flat engagement surfaces or edges that respectively engage in abutment with the lateral endo-cortex at the two distal locations.

The two distal locations of the lateral endo-cortex may be aligned in a common transverse plane of the subject's femur although this need not be the case.

In some embodiments, the distal end is interchangeable for selection and use of a distal tip for the femoral implant that is suitably shaped for the subject's anatomy.

In some embodiments, the femoral implant further includes a distal end angled in a sagittal plane of the subject's femur to enable improved alignment with the subject's femoral curvature when implanted therein. The distal end may be offset at an angle in a range of about 5 to 25 degrees, preferably about 10 to 20 degrees, and more preferably, approximately 15 degrees in the sagittal plane with respect to an elongate axis of the femoral implant. The distal end may be angled anteriorly in the sagittal plane with respect to the elongate axis of the femoral implant.

The femoral implant may further include a neck portion angled in a sagittal plane of the subject's femur to enable improved location of a femoral head of the implant with respect to the subject's femoral neck when implanted therein. Preferably, the neck portion is angled such that the femoral head is located posteriorly with respect to a central axis of the subject's femoral neck. The neck portion may be offset at an angle in a range of about 5 to 20 degrees, preferably about 5 to 15 degrees, and more preferably, approximately 10 degrees in the sagittal plane with respect to an elongate axis of the femoral implant. The neck portion may be angled posteriorly with respect to the elongate axis of the implant.

The femoral implant may be further configured for ease of removal from the subject's femur by including a bone in-growth coating suitably positioned for revision surgery. The coating may be positioned proximally about one-third medially and about one-half to two-thirds laterally so as to not obscure access to the femoral bone-implant interface distally during removal from the subject's femur.

In some embodiments, the femoral implant is configured to self-stabilise when implanted in the subject's femur such that micro-movement is reduced to no more than approximately 150 micrometres.

The femoral implant is configured for use as a short-stem prosthesis. The femoral implant may further be configured to preserve at least some of the subject's femoral neck when implanted therein. Thus, it may also be configured for use as a neck-preserving hip prosthesis.

Viewed from another aspect of the present invention, there is provided a short-stem femoral implant suitable for use in hip arthroplasty, the femoral implant having a distal end angled in a sagittal plane of the subject's femur to enable improved alignment with the subject's femoral curvature when implanted therein.

In some embodiments, the distal end may be offset at an angle in a range of about 5 to 25 degrees, preferably about 10 to 20 degrees, and more preferably, approximately 15 degrees in the sagittal plane with respect to an elongate axis of the femoral implant. The distal end may be angled anteriorly in the sagittal plane with respect to the elongate axis of the femoral implant.

The femoral implant may further include a neck portion angled in a sagittal plane of the subject's femur to enable improved location of a femoral head of the implant with respect to the subject's femoral neck when implanted therein. Preferably, the neck portion is angled such that the femoral head is located posteriorly with respect to a central axis of the subject's femoral neck. The neck portion may be offset at an angle in a range of about 5 to 20 degrees, preferably about 5 to 15 degrees, and more preferably, approximately 10 degrees in the sagittal plane with respect to an elongate axis of the femoral implant. The neck portion may be angled posteriorly with respect to the elongate axis of the implant.

The femoral implant may be further configured to self-stabilise against sliding across the endo-cortex when implanted in the subject's femur. The femoral implant may include a distal end configured to engage in abutment with the lateral endo-cortex of the subject's femur at two distal locations such that when implanted, the femoral implant has a reduced tendency for sliding across the endo-cortex.

In some embodiments, the distal end includes a flat abutment structure configured to engage in abutment with the lateral endo-cortex at the two distal locations. Alternatively, the distal end may include a contoured abutment structure configured to engage in abutment with the lateral endo-cortex at the two distal locations. In other embodiments, the distal end includes two rails forming an abutment structure, wherein the two rails each include flat engagement surfaces or edges that respectively engage in abutment with the lateral endo-cortex at the two distal locations.

The two distal locations of the lateral endo-cortex may be aligned in a common transverse plane of the subject's femur although this need not be the case.

In some embodiments, the femoral implant is further configured to self-stabilise against rotation about an elongate axis thereof when implanted in the subject's femur. The femoral implant may include a contoured surface having one or more recessed regions configured to distribute reaction forces imparted at the bone-implant interface such that when implanted, the femoral implant has a reduced tendency to rotate about the elongate axis.

Preferably, the one or more recessed regions are positioned on the femoral implant such that the reaction forces are transferred medially and/or laterally in a transverse plane of the subject's femur. The reaction forces may be transferred medially and/or laterally at successive levels along the elongate axis of the femoral implant. The one or more recessed regions may be positioned near or at a location where the femoral implant engages in abutment with the endo-cortex of the subject's femur. Preferably, the femoral implant includes two or more recessed regions on one or both of an anterior aspect and a posterior aspect of the femoral implant. The recessed regions may be formed in the contoured surface as one of: a bevel; a hollow; a flattened edge; a sloped edge; or a chamfer, and formed using manufacturing techniques known to a person skilled in the art.

In some embodiments, the distal end is interchangeable for selection and use of a distal tip for the femoral implant that is suitably shaped for the subject's anatomy.

The femoral implant may be further configured for ease of removal from the subject's femur by including a bone in-growth coating suitably positioned for revision surgery.

The coating may be positioned proximally about one-third medially and about one-half to two-thirds laterally so as to not obscure access to the femoral bone-implant interface distally during removal from the subject's femur.

In some embodiments, the femoral implant is configured to self-stabilise when implanted in the subject's femur such that micro-movement is reduced to no more than approximately 150 micrometres.

The femoral implant is configured for use as a short-stem prosthesis. The femoral implant may further be configured to preserve at least some of the subject's femoral neck when implanted therein. Thus, it may also be configured for use as a neck-preserving prosthesis.

Viewed from another aspect of the present invention, there is provided a short-stem femoral implant suitable for use in hip arthroplasty, the femoral implant having a neck portion angled in a sagittal plane of the subject's femur to enable improved location of a femoral head of the implant with respect to the subject's femoral neck when implanted therein.

Preferably, the neck portion is angled such that the femoral head is located posteriorly with respect to a central axis of the subject's femoral neck. The neck portion may be offset at an angle in a range of about 5 to 20 degrees, preferably about 5 to 15 degrees, and more preferably, approximately 10 degrees in the sagittal plane with respect to an elongate axis of the femoral implant. The neck portion may be angled posteriorly with respect to the elongate axis of the implant.

In some embodiments, the femoral implant further includes a distal end angled in a sagittal plane of the subject's femur to enable improved alignment with the subject's femoral curvature when implanted therein. The distal end may be offset at an angle in a range of about 5 to 25 degrees, preferably about 10 to 20 degrees, and more preferably, approximately 15 degrees in the sagittal plane with respect to an elongate axis of the femoral implant. The distal end may be angled anteriorly in the sagittal plane with respect to the elongate axis of the femoral implant.

The femoral implant may be further configured to self-stabilise against sliding across the endo-cortex when implanted in the subject's femur. The femoral implant may include a distal end configured to engage in abutment with the lateral endo-cortex of the subject's femur at two distal locations such that when implanted, the femoral implant has a reduced tendency for sliding across the endo-cortex.

In some embodiments, the distal end includes a flat abutment structure configured to engage in abutment with the lateral endo-cortex at the two distal locations. Alternatively, the distal end may include a contoured abutment structure configured to engage in abutment with the lateral endo-cortex at the two distal locations. In other embodiments, the distal end includes two rails forming an abutment structure, wherein the two rails each include flat engagement surfaces or edges that respectively engage in abutment with the lateral endo-cortex at the two distal locations.

The two distal locations of the lateral endo-cortex may be aligned in a common transverse plane of the subject's femur although this need not be the case.

In some embodiments, the femoral implant is further configured to self-stabilise against rotation about an elongate axis thereof when implanted in the subject's femur. The femoral implant may include a contoured surface having one or more recessed regions configured to distribute reaction forces imparted at the bone-implant interface such that when implanted, the femoral implant has a reduced tendency to rotate about the elongate axis.

Preferably, the one or more recessed regions are positioned on the femoral implant such that the reaction forces are transferred medially and/or laterally in a transverse plane of the subject's femur. The reaction forces may be transferred medially and/or laterally at successive levels along the elongate axis of the femoral implant. The one or more recessed regions may be positioned near or at a location where the femoral implant engages in abutment with the endo-cortex of the subject's femur. Preferably, the femoral implant includes two or more recessed regions on one or both of an anterior aspect and a posterior aspect of the femoral implant. The recessed regions may be formed in the contoured surface as one of: a bevel; a hollow; a flattened edge; a sloped edge; or a chamfer, and formed using manufacturing techniques known to a person skilled in the art.

In some embodiments, the distal end is interchangeable for selection and use of a distal tip for the femoral implant that is suitably shaped for the subject's anatomy.

The femoral implant may be further configured for ease of removal from the subject's femur by including a bone in-growth coating suitably positioned for revision surgery. The coating may be positioned proximally about one-third medially and about one-half to two-thirds laterally so as to not obscure access to the femoral bone-implant interface distally during removal from the subject's femur.

In some embodiments, the femoral implant is configured to self-stabilise when implanted in the subject's femur such that micro-movement is reduced to no more than approximately 150 micrometres.

The femoral implant is configured for use as a short-stem prosthesis. The femoral implant may further be configured to preserve at least some of the subject's femoral neck when implanted therein. Thus, it may also be configured for use as a neck-preserving prosthesis.

Viewed from another aspect of the present invention, there is provided a short-stem femoral implant suitable for use in hip arthroplasty, the femoral implant configured for ease of removal from the subject's femur by including a bone in-growth coating suitably positioned for revision surgery, wherein the coating is positioned proximally about one-third medially and about one-half to two-thirds laterally so as to not obscure access to the femoral bone-implant interface distally during removal from the subject's femur.

In some embodiments, the bone in-growth coating is suitably positioned for revision surgery as well as to provide maximally physiological loading of bone in the proximal femur. This advantageously ensures that there is distribution of load through the in-grown bone to prevent stress-shielding of bone in the proximal femur.

In some embodiments, the femoral implant is further configured to self-stabilise against sliding across the endo-cortex when implanted in the subject's femur. The femoral implant may include a distal end configured to engage in abutment with the lateral endo-cortex of the subject's femur at two distal locations such that when implanted, the femoral implant has a reduced tendency for sliding across the endo-cortex.

In some embodiments, the distal end includes a flat abutment structure configured to engage in abutment with the lateral endo-cortex at the two distal locations. Alternatively, the distal end may include a contoured abutment structure configured to engage in abutment with the lateral endo-cortex at the two distal locations. In other embodiments, the distal end includes two rails forming an abutment structure, wherein the two rails each include flat engagement surfaces or edges that respectively engage in abutment with the lateral endo-cortex at the two distal locations.

The two distal locations of the lateral endo-cortex may be aligned in a common transverse plane of the subject's femur although this need not be the case.

In some embodiments, the distal end is interchangeable for selection and use of a distal tip for the femoral implant that is suitably shaped for the subject's anatomy.

In some embodiments, the femoral implant is further configured to self-stabilise against rotation about an elongate axis thereof when implanted in the subject's femur. The femoral implant may include a contoured surface having one or more recessed regions configured to distribute reaction forces imparted at the bone-implant interface such that when implanted, the femoral implant has a reduced tendency to rotate about its elongate axis.

Preferably, the one or more recessed regions are positioned on the femoral implant such that the reaction forces are transferred medially and/or laterally in a transverse plane of the subject's femur. The reaction forces may be transferred medially and/or laterally at successive levels along the elongate axis of the femoral implant. The one or more recessed regions may be positioned near or at a location where the femoral implant engages in abutment with the endo-cortex of the subject's femur. Preferably, the femoral implant includes two or more recessed regions on one or both of an anterior aspect and a posterior aspect of the femoral implant. The recessed regions may be formed in the contoured surface as one of: a bevel; a hollow; a flattened edge; a sloped edge; or a chamfer, and formed using manufacturing techniques known to a person skilled in the art.

In some embodiments, the femoral implant further includes a distal end or tip that is angled in a sagittal plane of the subject's femur to enable improved alignment with the subject's femoral curvature when implanted therein. The distal end or tip may be offset at an angle in a range of about 5 to 25 degrees, preferably about 10 to 20 degrees, and more preferably, approximately 15 degrees in the sagittal plane with respect to an elongate axis of the femoral implant. The distal end may be angled anteriorly in the sagittal plane with respect to the elongate axis of the femoral implant.

The femoral implant may further include a neck portion angled in a sagittal plane of the subject's femur to enable improved location of a femoral head of the implant with respect to the subject's femoral neck when implanted therein. Preferably, the neck portion is angled such that the femoral head is located posteriorly with respect to a central axis of the subject's femoral neck. The neck portion may be offset at an angle in a range of about 5 to 20 degrees, preferably about 5 to 15 degrees, and more preferably, approximately 10 degrees in the sagittal plane with respect to an elongate axis of the femoral implant. The neck portion may be angled posteriorly with respect to the elongate axis of the implant.

In some embodiments, the femoral implant is configured to self-stabilise when implanted in the subject's femur such that micro-movement is reduced to no more than approximately 150 micrometres.

The femoral implant is configured for use as a short-stem prosthesis. The femoral implant may further be configured to preserve at least some of the subject's femoral neck when implanted therein. Thus, it may also be configured for use as a neck-preserving prosthesis.

Viewed from another aspect of the present invention, there is provided a short-stem hip prosthesis suitable for use in hip arthroplasty, the hip prosthesis including the femoral implant according to any one of the aspects of the present invention as described herein.

Viewed from yet another aspect of the present invention, there is provided a modular distal tip configured for use with a short-stem femoral implant, the modular distal tip being adapted to couple with the femoral implant, and configured to engage in abutment with a lateral endo-cortex of a subject's femur at two distal locations such that when implanted, the femoral implant has a reduced tendency for sliding across the endo-cortex.

In some embodiments, the modular distal tip includes a flat abutment structure configured to engage in abutment with the lateral endo-cortex at the two distal locations. Alternatively, the modular distal tip may include a contoured abutment structure configured to engage in abutment with the lateral endo-cortex at the two distal locations. In other embodiments, the modular distal tip includes two rails forming an abutment structure, wherein the two rails each include flat engagement surfaces or edges that respectively engage in abutment with the lateral endo-cortex at the two distal locations.

The two distal locations of the lateral endo-cortex may be aligned in a common transverse plane of the subject's femur although this need not be the case.

In some embodiments, the modular distal tip is angled in a sagittal plane of the subject's femur to enable improved alignment with the subject's femoral curvature when implanted therein. The distal tip may be offset at an angle in a range of about 5 to 25 degrees, preferably about 10 to 20 degrees, and more preferably, approximately 15 degrees in the sagittal plane with respect to an elongate axis of the femoral implant. The distal end may be angled anteriorly in the sagittal plane with respect to the elongate axis of the femoral implant.

BRIEF DESCRIPTION OF DRAWINGS

The invention will now be described in greater detail with reference to the accompanying drawings in which like features are represented by like numerals. It is to be understood that the embodiments shown are examples only and are not to be taken as limiting the scope of the invention as defined in the claims appended hereto.

FIGS. 6a to 6d show cross-sections of the prosthetic femoral implant of FIG. 5 through the lines a-a', b-b', c-c' and d-d', respectively. The top of each Figure corresponds to the lateral side of the subject's left femur. FIG. 6d shows variations of a modified distal tip according to embodiments of the invention.

FIGS. 9a to 9c illustrate, respectively, a flat abutment structure, a contoured abutment structure, and two rails forming an abutment structure with respective flat engagement surfaces.

FIGS. 11a and 11b further show the modified distal tip with the abutment structure of FIGS. 9b and 9c, respectively.

DETAILED DESCRIPTION

Embodiments of the invention are discussed herein by reference to the drawings which are not to scale and are intended merely to assist with explanation of the invention. Anatomical terms and planes recited throughout this specification are defined with respect to a subject's femur. The relevant anatomical terms referred to include posterior, anterior, medial, lateral, distal and proximal, and the relevant anatomical planes referred to include the sagittal or anterior-posterior plane, the transverse or horizontal plane, and the coronal or medial-lateral plane. The lateral view refers to the view from the lateral side of the subject's femur (in the anterior-posterior plane). The frontal view refers to the view from the anterior aspect of the subject's femur (in the medial-lateral plane).

The invention has particular utility in short-stem hip prostheses for use in hip arthroplasty. More particularly, the femoral implant of the invention has utility in femoral neck-preserving short-stem hip prostheses. The specification and drawings describe embodiments of the invention with reference to a femoral implant and hip prosthesis suitable for implantation in a subject's left femur of a left hip joint. However, embodiments of the invention are not limited to this application, and are also suitable for implantation in a subject's right femur of a right hip joint.

The inventive femoral implant disclosed herein has been developed by the inventor to improve upon or at least ameliorate the short-comings of known short-stem hip prostheses, especially insofar as they suffer from subsidence after implantation. The inventor has determined that subsidence of femoral stems results at least in part from lack of stability of the implanted femoral stem, especially during (i) initial impaction and immediately post-implantation, and (ii) early post-operative use of the prosthesis by the subject before bone in-growth occurs. The inventor has evaluated that the instability during these periods is a result of the design of existing short-stem femoral components.

Accordingly, the inventor proposes a novel prosthetic femoral implant to address problems with the existing design in order to maximise the stability of the implanted femoral stem, before bone in-growth occurs and therefore to reduce the risk of subsidence. In order to appreciate the significance of the inventor's findings, fixation of femoral stems in existing short-stem hip prostheses will firstly be described.

Fixation of Existing Femoral Stems

Figure 1:
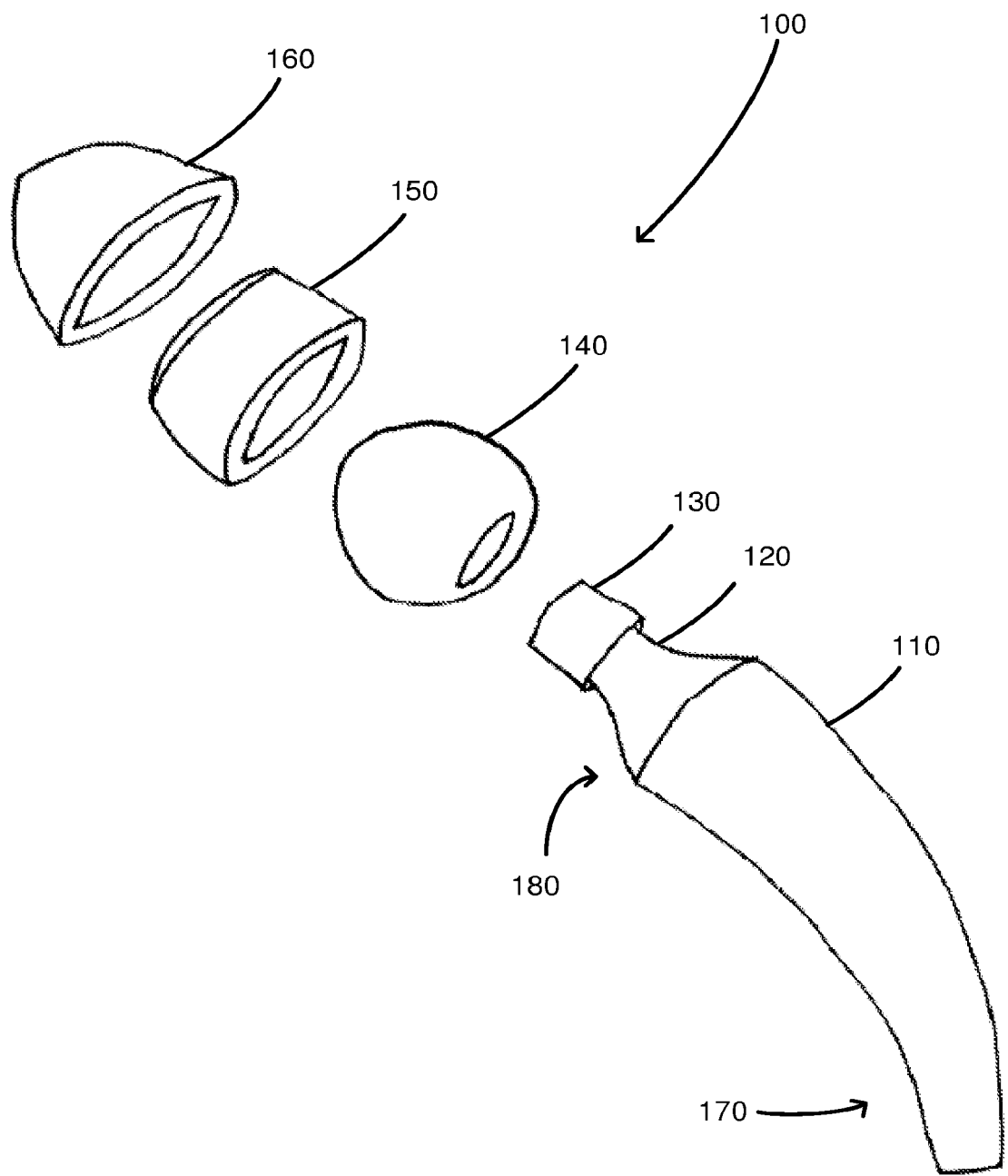
FIG. 1 illustrates an exploded view of the components of a prior art short-stem hip prosthesis.
Figure 2:
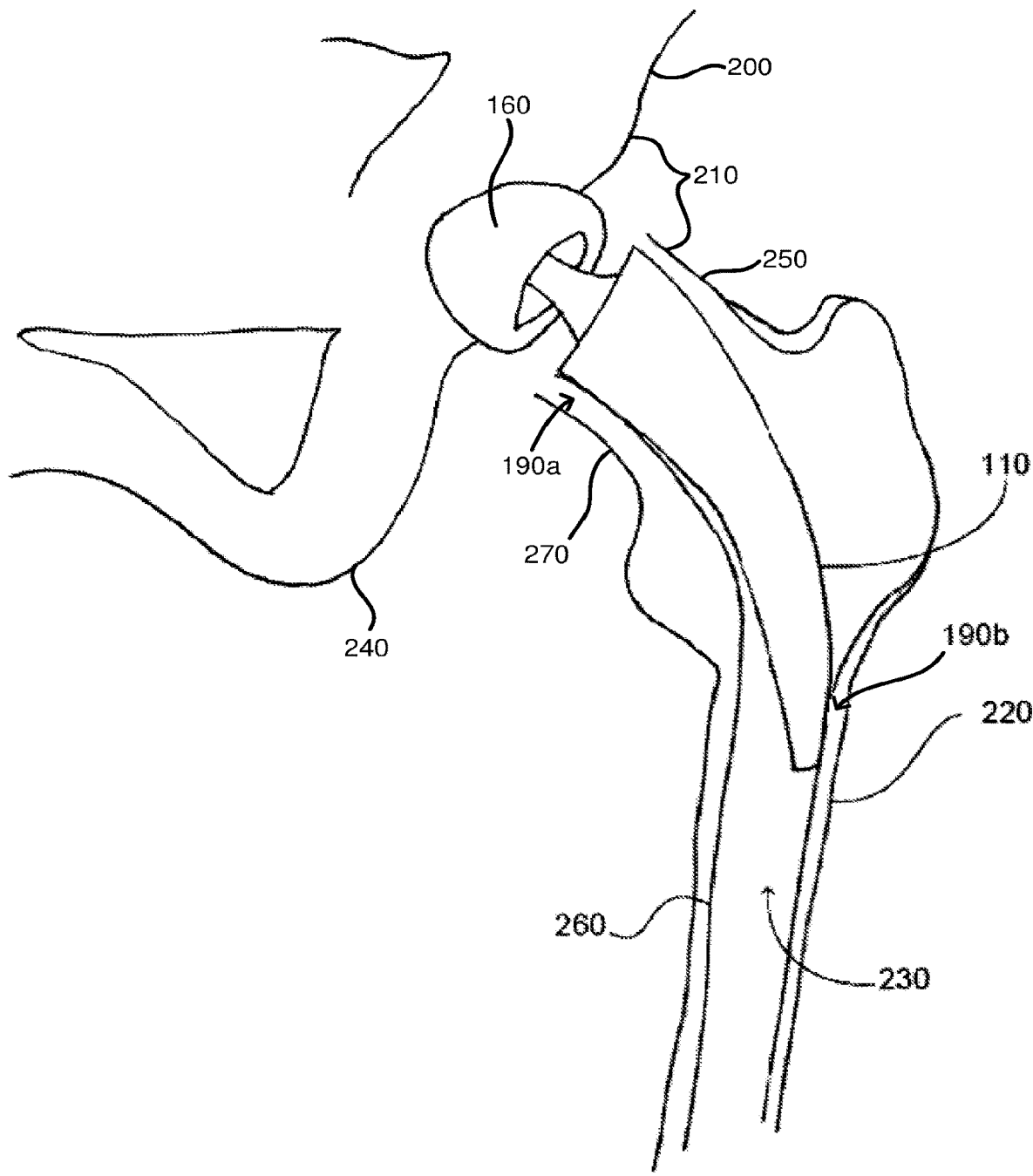
FIG. 2 illustrates a frontal view of the prior art short-stem hip prosthesis of FIG. 1 implanted within a subject's left femur, when the subject is stationery and standing, showing preserved bone of the femoral neck.

FIG. 1 illustrates the components of an existing short-stem hip prosthesis 100 in an exploded schematic view. The hip prosthesis 100 includes a femoral stem 110 with neck portion 120 and trunion 130, a femoral head 140, an acetabular cup liner 150 and an acetabular cup 160. The positioning of the hip prosthesis 100 when implanted in a subject 200 following total hip arthroplasty (THA) is illustrated in FIG. 2, which is a frontal view of a coronal section of the subject's left hip 210, (when the subject 200 is stationery and standing). The femoral stem 110 is implanted proximally within a prepared left femur 220 of the subject 200. The acetabular cup liner 150 and cup 160 are implanted within a prepared acetabulum 240 of the subject 200 (not shown). The femoral head 140 is positioned on the trunion 130 of the prosthetic femoral stem 110 and the acetabular cup liner 150 and acetabular cup 160 are positioned in the bony pelvis. After reduction of the hip 210, articulation occurs between the prosthetic head 140 and the liner 150.

Advantageously, the prosthetic femoral stem 110 allows the distal half to two thirds of the subject's femoral neck 250 to be preserved during THA, as shown in FIG. 2. The prosthetic femoral stem 110 also includes a double taper of an elliptical, rhomboidal or complex cross-section, such that its cross-section reduces in area from the proximal end 180 to the distal end 170 of the prosthetic femoral stem 110. The double taper aims to stabilise the implanted femoral stem 110 through taper-fit fixation within the subject's cortical and cancellous femoral bone. The prosthetic femoral stem 110 also includes a curvature to facilitate accommodation of the femoral stem 110 proximally within the subject's femur 220 as shown in the frontal view of FIG. 2. The curvature aims to stabilise the implanted femoral stem 110 by enabling opposing sides to sit within and in abutment with the internal surface (or endo-cortex 260) of the subject's femur 220 at various locations.

The left hip 210 illustrated in FIG. 2 may have a femoral morphology described as neutral, anteverted or retroverted depending on the anatomical structure of the subject 200. Anteversion of the femur is by far the most common anatomical variant. Accordingly, the known prosthetic femoral stem 110 and inventive femoral implant 410 will be described herein with reference to femora that are normally anteverted. However, neutral and retroverted femora are also mentioned for completeness.

Figure 4:
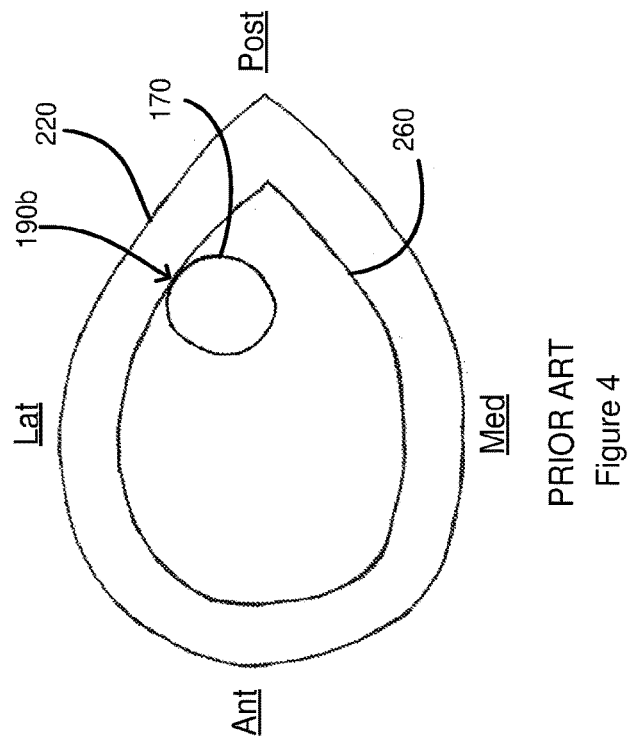
FIG. 4 shows a cross-section of the distal tip of the prior art prosthetic femoral stem of FIG. 3 through the lines 3-3'. The top of the Figure corresponds to the lateral side of the subject's left femur.
Figure 3:
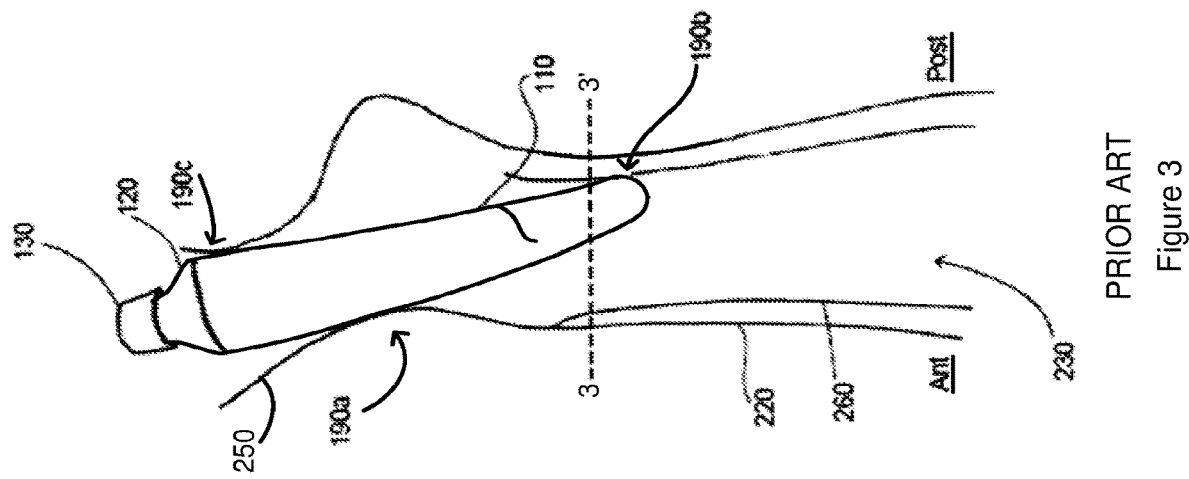
FIG. 3 illustrates a lateral view of the prior art prosthetic femoral stem of FIG. 1 implanted within a subject's left femur, which is normally anteverted.

FIG. 3 illustrates the positioning of the known prosthetic femoral stem 110 when implanted within a subject's left femur 220, which is normally anteverted. FIG. 3 shows a lateral view through the anterior-posterior plane of the subject's femur 220, where reference numerals 190*a*, 190*b* and 190*c* designate the approximate locations where abutment fixation between the femoral stem 110 and the endo-cortex 260 occurs. Anteversion is characterised by posterior-anterior-posterior (PAP) endo-cortical engagement as shown in FIG. 3. In particular, the prosthetic femoral stem 110 is only fixed by distal "one-point abutment" with respect to the endo-cortex 260 at 190*b*. This is further illustrated in FIG. 4, which is a cross-sectional view of the distal end 170 of the prosthetic femoral stem 110 through the lines 3-3' of FIG. 3. For anteverted femora, the distal end 170 is positioned postero-laterally and abuts with the endo-cortex at 190*b* as shown in FIG. 4.

In contrast, where there is retroversion of the femur (not shown), anterior-posterior-anterior (APA) endo-cortical engagement occurs. Subjects 200 with neutral version femora (not shown) do not have this three-point engagement. Rather, the femoral stem 110 co-aligns with or better enjoys taper-fit with the endo-cortex 260 of the femoral neck 250.

In addition to endo-cortical engagement in the anteverted or retroverted femur 220, there is taper-fit fixation of the implanted prosthetic femoral stem 110 within the cortex of the subject's femoral neck 250 and within the cancellous bone. A normally anteverted femur has poorly aligned endo-cortical taper-fit fixation of the prosthetic femoral stem 110 within the subject's femoral neck 250 due to a mismatch between the subject's anatomy and the implant 110. This is shown in FIG. 3 by the imperfect alignment of the prosthetic femoral stem 110 within the subject's femoral neck 250. Subjects 200 with neutral version femora (not shown) enjoy better aligned taper-fit of the prosthetic femoral stem 110 within the endo-cortex of the subject's femoral neck 250 (but do not enjoy APA or PAP three-point endo-cortical engagement).

1. Torsional Forces During Impaction

During impaction, the prosthetic femoral stem 110 is implanted in the subject's prepared femur 220 by gentle hammering until fixation of the femoral stem 110 is achieved. Taper-fit fixation occurs in cancellous bone surrounding the prosthetic femoral stem 110 as it becomes positioned within the subject's femur 220. At or near final impaction, there is endo-cortical engagement of the distal end 170 which abuts laterally against the endo-cortex 260. This engagement is illustrated in FIGS. 2 and 3 through abutment fixation point 190*b*.

Torsional forces are induced at the bone-implant interface at final impaction. The torsional forces arise due to the reaction forces imparted at the cortical bone-implant interface along the curved elongate axis of the femoral stem 110. These reaction forces occur predominately at the locations of the PAP and APA endo-cortical engagement within anteverted and retroverted femora, respectively. Reaction forces occur at the bone-implant interface at every point where fixation forces have been imparted. Every cross-section of the femoral stem 110 in the transverse plane of the subject's femur 220 will have a net reaction force.

Physiological loading can induce forces which can cause the femoral stem 110 to "spin" or rotate, thus causing rotational instability around the elongate axis, or the line or direction of impaction of the prosthetic femoral stem 110, i.e. within the subject's femoral neck 250. As a result, rotational instability of the prosthetic femoral stem 110 may occur immediately after implantation which, if left unresolved, can worsen causing mechanical failure. This may result in failure (by subsidence) of the short-stem hip prosthesis 100.

Surface Contours to Reduce Torsional Forces

To address this problem, the invention provides an inventive prosthetic femoral implant 410 that is configured to self-stabilise against rotation about an elongate axis thereof when implanted in a subject's femur 220. The femoral implant 410 ideally includes a contoured surface for improved stability during impaction. This feature can also aid stability during recovery and initial mobilisation. The inventor has developed a prosthetic femoral implant 410 configured with surface contours that modify reaction force vectors between the bone and implant 410. Ideally, the contoured surface includes two or more regions of the femoral implant 410 in engagement with the endo-cortex 260 of the subject's femoral shaft 230, that are "flattened" or recessed such that the cross-section at certain sections is altered. The result is a cross-sectional profile that is somewhat irregular along the length of the femoral implant 410 with the irregularities formed such that the effect is to re-distribute the net reaction forces along the elongate axis of the implant 410, to mitigate "spin" without reducing the implant's elongate curvature.

Figure 5:
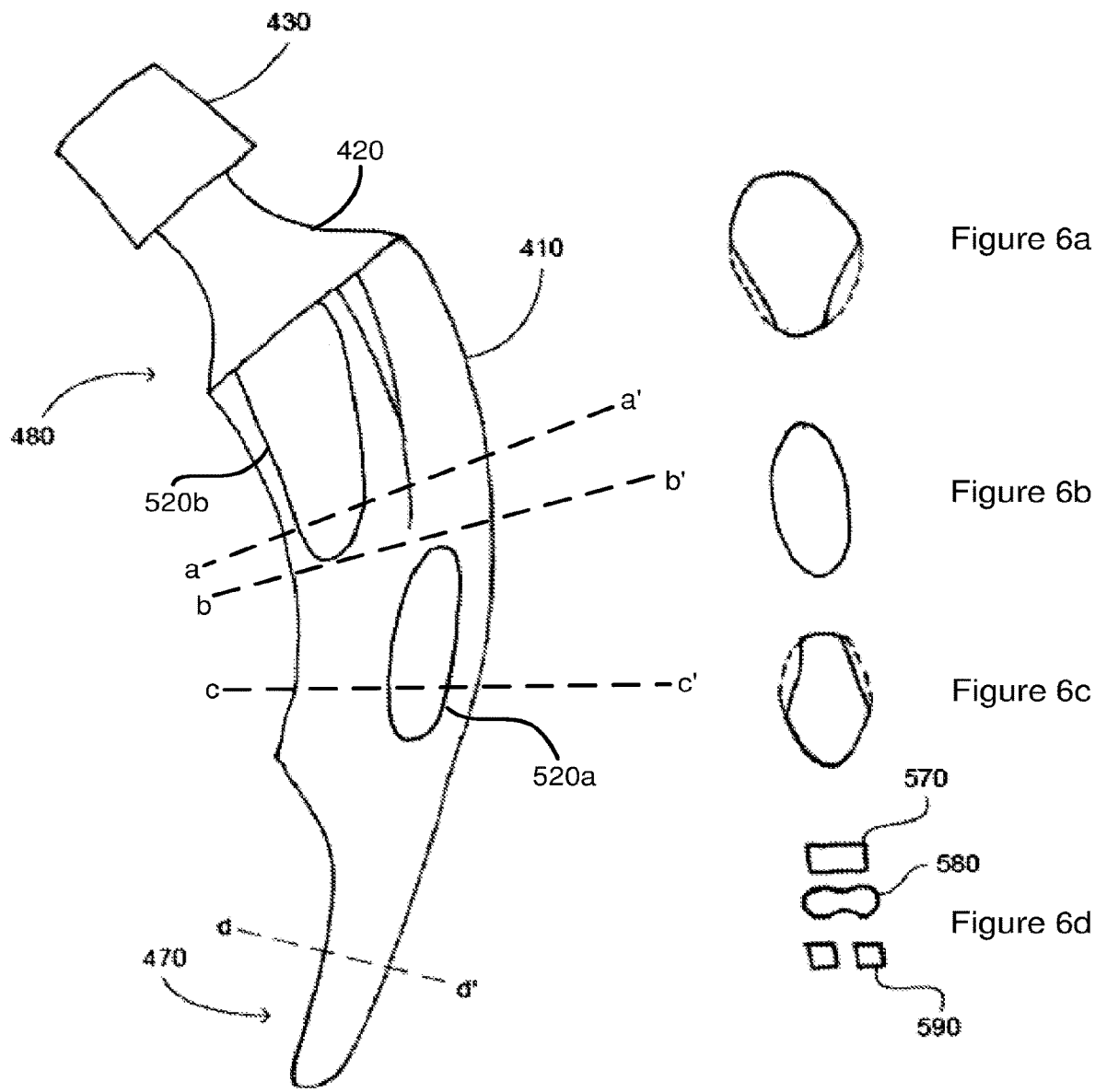
FIG. 5 illustrates a frontal view of a femoral implant according to an embodiment of the invention, showing recessed regions in a contoured surface of the femoral implant.

In a preferred embodiment of the invention, there is provided a prosthetic femoral implant 410 which includes contoured or recessed regions 520*a* and 520*b* on anterior and posterior aspects of the femoral implant 410. FIG. 5 is a frontal view of the prosthetic femoral implant 410 which includes such recessed regions 520*a* and 520*b* on the anterior aspect. Preferably, the recessed regions 520*a* and 520*b* are positioned on the femoral implant 410 at approximately the level of abutment with the endo-cortex where PAP endo-cortical engagement occurs. For example, the recessed region 520*a* is ideally positioned between about one-third and two-thirds proximally and about one-third laterally on the femoral implant 410, and the recessed region 520*b* is ideally positioned about one-third proximally and about one-third medially on the femoral implant 410. Although not shown in FIG. 5, the recessed regions are also preferably positioned on the posterior aspect of the prosthetic femoral implant 410 such that they are in mirror image with the recessed regions on the anterior aspect. Accordingly, the prosthetic femoral implant 410 may preferably include four recessed regions (two shown). Although the femoral implant 410 is described as having at least two recessed regions, the femoral implant 410 may only include one recessed region, or alternatively, between one and four recessed regions, or any number of recessed regions.

FIGS. 6*a* to 6*d* show cross-sections of the prosthetic femoral implant 410 of FIG. 5 through the lines a-a', b-b', c-c' and d-d'. Lines a-a' and c-c' transect the recessed regions 520*b* and 520*a*, whereas lines b-b' and d-d' transect non-contoured regions of the femoral implant 410. The top of each of FIGS. 6a to 6c corresponds to the lateral aspect of the prosthetic femoral implant 410. In particular, FIGS. 6a to 6c illustrate the varying cross-section of the inventive prosthetic femoral implant 410 as a result of the recessed regions 520a and 520b. The recessed regions 520a, 520b may be formed in the contoured surface as one of: a bevel, a hollow, a flattened edge, a sloped edge or a chamfer so as to contour a femoral implant 410 otherwise having a generally elliptical (or e.g., rhomboidal or complex) cross-section along its length. Additionally/alternatively, recessed regions 520a, 520b may be achieved through manufacturing processes known to a person skilled in the art.

Figure 7:
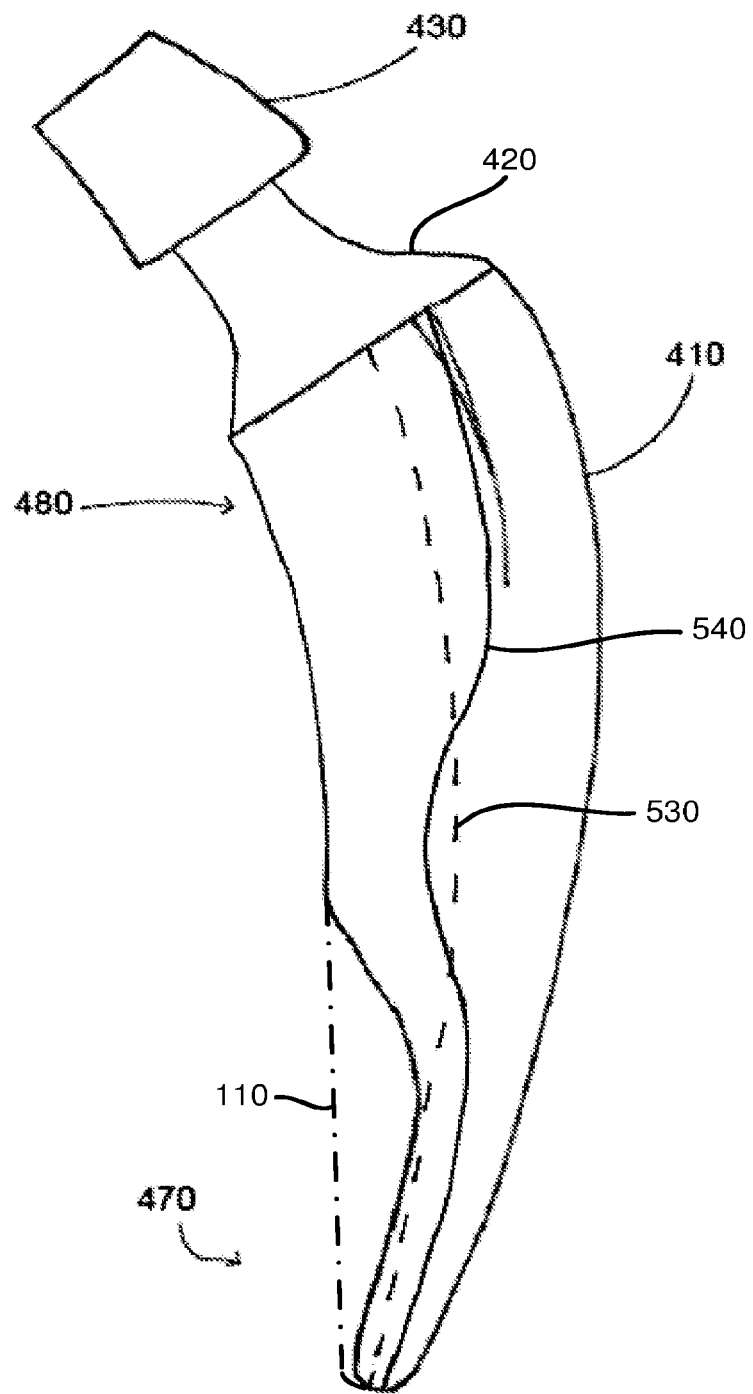
FIG. 7 shows the prosthetic femoral implant of FIG. 5 (but not showing the recessed regions) overlaid with the prior art prosthetic femoral stem of FIG. 1 in broken lines, illustrating redistribution of the net reaction forces at the bone-implant interface along the elongate axis of the implant according to an embodiment of the invention.

FIG. 7 is a schematic illustration demonstrating that provision of recessed regions 520a, 520b on the anterior aspect, and preferably, also on the posterior aspect (not shown) on the prosthetic femoral implant 410, as well as tapering of the distal end 470 of the implant 410, re-distributes the net reaction forces on the surface of the implant 410 which in turn reduces the tendency for rotation to be induced in the subject's femoral shaft 230 and neck 250 during the final stage of initial impaction. FIG. 7 shows a frontal view of the inventive prosthetic femoral implant 410 of FIG. 5 in solid lines but in the absence of the recessed regions 520a and 520b for clarity purposes. Overlaid is an outline of the prior art prosthetic femoral stem 110 of FIG. 1 shown in broken lines, and illustrated by the larger width of the distal tip at distal end 470).

The lines 530 and 540 represent the approximate location of the transverse component of the net reaction force on the anterior aspect of the existing femoral stem 110 and inventive femoral implant 410, respectively. Although not shown, the transverse component of the net reaction force will be similarly located on the respective posterior aspect of the stem 110 and implant 410. Curved line 530 generally follows the curvature of the existing femoral stem 110. However, as a result of modifying the surface of the inventive prosthetic femoral implant 410 by incorporating recessed regions 520a and 520b, the line 540 no longer follows the same curvature. The location of the line 540 of net reaction force has been shifted medially in relation to recessed region 520a, laterally in relation to recessed region 520b and laterally in relation to the tapered distal end 470. The overall result is a re-distribution of the net reaction forces, such that torsional forces induced by PAP or APA endo-cortical engagement in anteverted and retroverted femora, respectively, during final impaction, are substantially reduced.

2. Movement of Distal Tip During Physiological Loading

The existing short-stem hip prosthesis 100 is a cementless implant and usually includes a porous coating to encourage bone in-growth into the prosthetic femoral stem 110. The bone in-growth provides long-term fixation and stability of the prosthetic femoral stem 110 within the subject's femur 220. However, the surrounding bone of the prepared proximal femur 220 takes several weeks to fully grow into the porous coating. Accordingly, it is only the taper-fit fixation and endo-cortical engagement of the prosthetic femoral stem 110 within the subject's femur 220 that provides stability during this time. The endo-cortical engagement will now be described in more detail.

When the subject 200 is stationery and standing, the prosthetic femoral stem 110 implanted in the subject's femur 220 is stabilised through two-point endo-cortical abutment fixation, as shown in the frontal view of FIG. 2. A gravitational force is transferred through the head 140 and neck 120 of the prosthetic femoral stem 110 to the proximal end 180. This is balanced by a reaction force from the distal end 170 applied through two abutment points 190a and 190b. The first abutment point 190a is located towards the proximal end 180 of the femoral stem 110 and medially engages the calcar 270. The second abutment point 190b is located towards the distal end 170 of the femoral stem 110 and laterally engages the endo-cortex 260. The reaction forces provided at the two abutment points 190a and 190b effectively stabilise and prevent the prosthetic femoral stem 110 from moving in the coronal plane of subject's left femur 220.

However, when the subject 200 is seated or walking, the "one point abutment" at 190b achieved with existing short femoral stems 110 is insufficient to stabilise the distal end 170 in the coronal plane before bone in-growth has occurred. This is due to loading of the femoral stem 110 at an angle or in the transverse plane of the subject's femur 220. Consequently, the distal end 170 of the prosthetic femoral stem 110 may "slide" or "lift-off" in the sagittal plane of the subject's femur 220 due to physiological loading/unloading, and gravitational or physiological forces.

The inventor has deduced that the main reason for the lack of fixation is due to the shape of the surface of the prosthetic femoral stem 110 in engagement with the lateral endo-cortex 260 (e.g. at the second abutment point 190b). Existing prosthetic short femoral stems 110 include a double tapered ellipse, rhomboid, or complex combination of both. The resulting cross-section is generally identical in shape although decreasing in area along the length of the femoral stem 110. Some existing short femoral stems 110 have a pointed tip to increase the taper.

Returning now to FIG. 4, illustrating the cross-section of the existing prosthetic femoral stem 110 of FIG. 3 through the lines 3-3, the femoral stem 110 is only fixed by distal "one-point abutment" with respect to the endo-cortex 260 at 190b due to its cross-sectional shape, which in this example is circular. This fixation is inadequate because the distal end 170 can move fore and aft (anteriorly or posteriorly) across the lateral endo-cortex 260. Movement of the distal end 170 of the prosthetic femoral stem 110 across the lateral endo-cortex 260 signifies the presence of micro-movement in what could be characterised as a "windscreen wiper effect". Micro-movement can cause abrasive destruction of bone, especially the bone surrounding the areas of porous coating, failure of bone in-growth into the areas of the implant having porous coating, implant loosening and subsidence. Accordingly, physiological loading may then result in subsidence of the femoral stem 110 within the subject's femur 220, and ultimately result in failure of the short-stem hip prosthesis 100.

Modified Distal Tip with Two-Point Fixation

In order to address this potential source of instability, an inventive prosthetic femoral implant 410 is proposed that is configured to self-stabilise against sliding across the endo-cortex 260 when implanted in a subject's femur 220. The femoral implant 410 is ideally configured to engage distally within the prepared femoral shaft 230 of the subject 200 to stabilise the femoral implant 410 in the sagittal plane when implanted in the subject's femur 220, and reduce its tendency for sliding across the endo-cortex 260. Ideally, prosthetic femoral implant 410 includes or couples with a modified distal end or tip 470 that stabilises the prosthetic femoral implant 410 through endo-cortical abutment at or along two distal locations, at or near the lateral or postero-lateral aspect. This improves upon one-point distal abutment fixation provided at abutment point 190b in prior art prosthetic femoral stems 110. Advantageously, modification of the distal end or tip provides stability during physiological loading of the prostheses post-implantation, by reducing "wind-shield wiper" movement of the distal stem within the femur 220.

Figure 8:
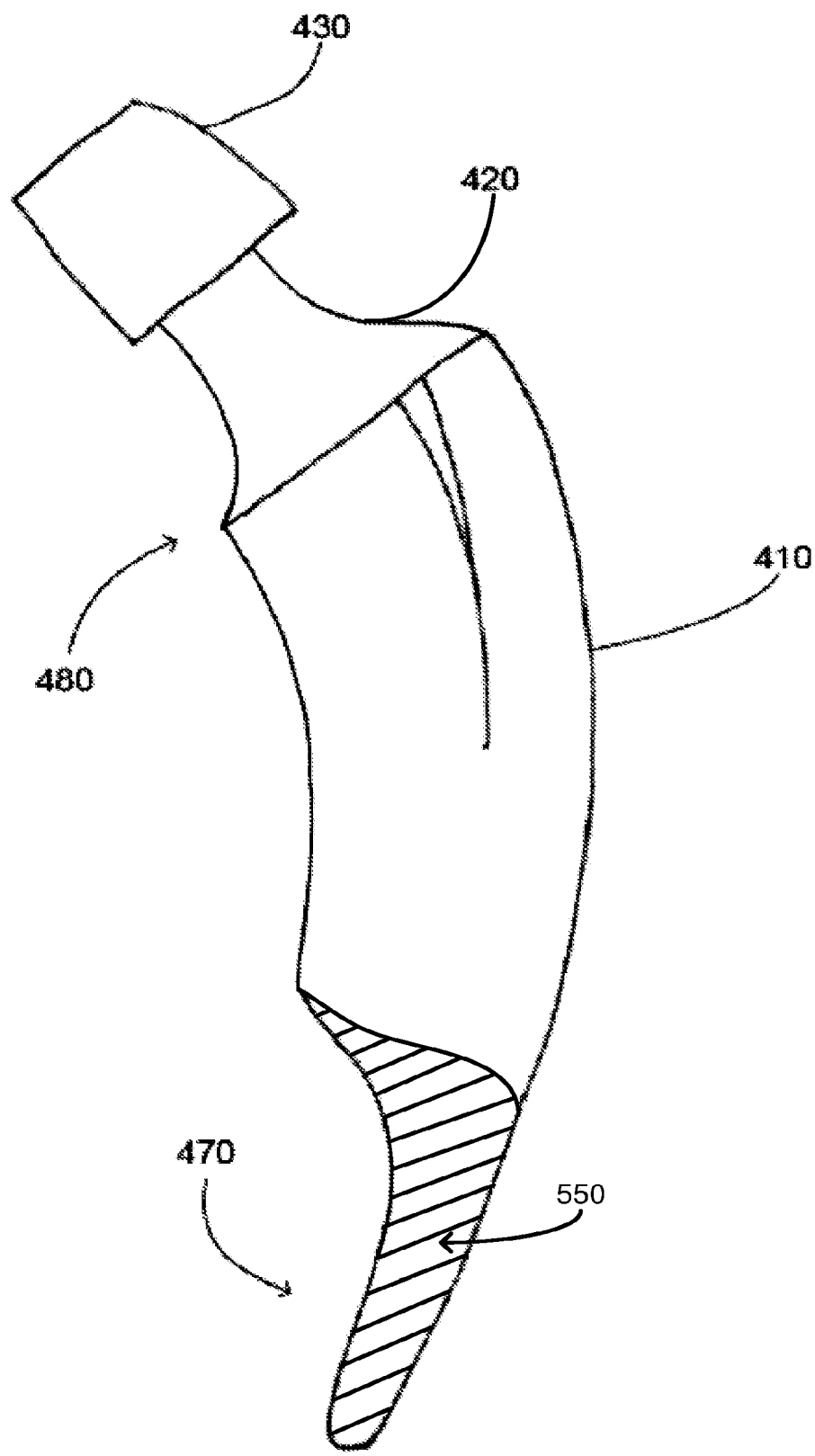
FIG. 8 illustrates a frontal view of a femoral implant according to an embodiment of the invention, showing a modified distal tip.

FIG. 8 illustrates a frontal view of a preferred embodiment of the invention which provides prosthetic femoral implant 410 with a modified distal end 470 and modified distal tip 550. The modified distal end 470 with tip 550 includes an abutment structure that, instead of continuing the elliptical or rhomboidal or other tapered cross-sectional shape, is shaped to sit in abutment with the endo-cortex 260 at two locations. The modified distal end 470 has a wider anterior-posterior dimension than medial-lateral, which is in contrast to the distal end 170 of the existing femoral stem 110, which often have a wider medial-lateral dimension, or extremely tapered femoral stem design with a small square or circular cross-section. The present invention advantageously stabilises the prosthesis in the sagittal plane, such that it is more stable when the subject is seated or walking by preventing anterior/posterior movement.

The modified distal tip 550 may be modular and interchangeable with the remainder of the prosthetic femoral implant 410 (not shown). Attachment may be through screws, friction fit, threaded join or other fixation means as would be known to a person skilled in the art and which are sufficient to ensure stable attachment, before and during implantation in the subject's femur 220 and post operatively. Alternatively, the modified distal tip 550 may be integral with the prosthetic femoral implant 410 ("mono-block" as shown).

Figure 9A:
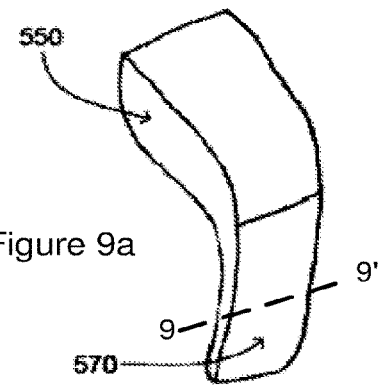
FIGS. 9a to 9c show variations of the modified distal tip of FIG. 8.
Figure 10A:
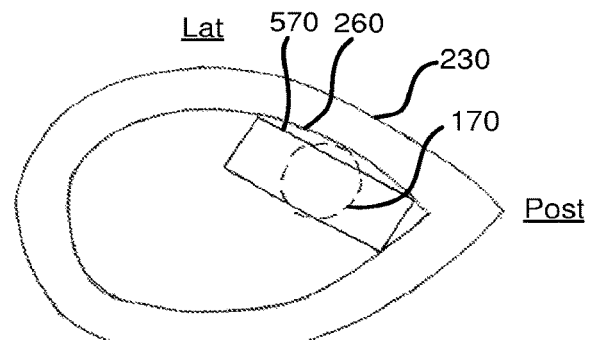
FIGS. 10a to 10c show cross-sections of the modified distal tips of FIGS. 9a to 9c through the lines 9-9' when implanted in a subject's left femur. The top of each Figure corresponds to the lateral side of the femur. The broken lines illustrate the cross-section of the prior art distal tip of FIG. 4 for comparison with the modified distal tips of embodiments of the invention.
Figure 9B:
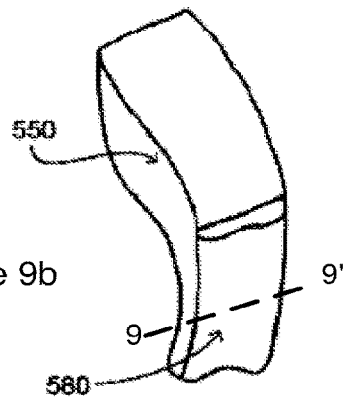
Figure 10B:
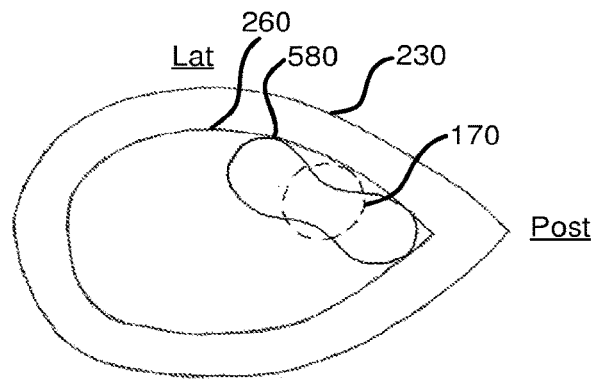
Figure 9C:
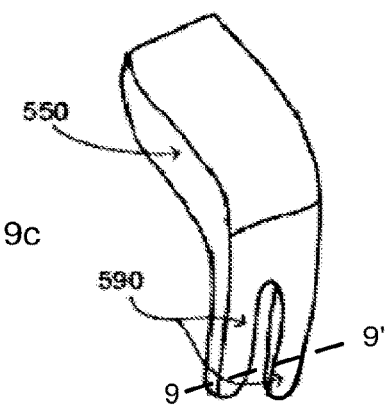
Figure 10C:
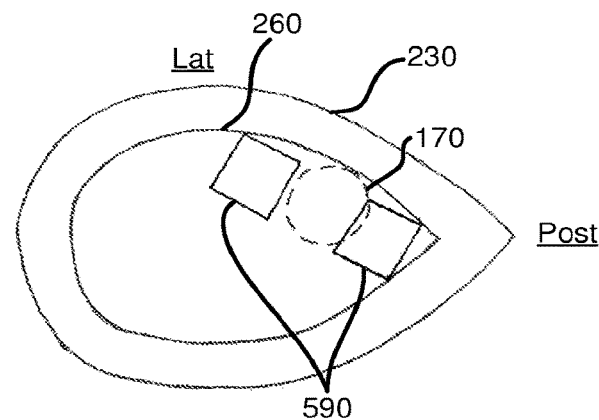

Embodiments of the modified distal tip 550 are illustrated in perspective views in FIGS. 9a to 9c. The modified distal tip 550 includes an abutment structure configured to provide (lateral) endo-cortical abutment fixation at two locations. FIGS. 9a to 9c illustrate abutment structures 570, 580 and 590 on a modular modified distal tip 550 although the abutment structures shown may be incorporated into the distal end 470 of a unitary inventive femoral implant 410. FIGS. 10a to 10c show cross-sections through the lines 9-9' of each of FIGS. 9a to 9c, respectively, once positioned within the subject's femoral shaft 230, for a subject 200 with an anteverted femur 220. The top of each Figure corresponds to the lateral side of the subject's left femur 220. The broken lines illustrate the prior art distal end or tip 170 as shown and discussed above in relation to FIG. 4, for comparison with the dual distal abutment locations of the modified distal tip 550.

FIG. 9a shows a flat abutment structure 570 with a finely tapered cross-section and flat curved surface that engages the endo-cortex 260. As shown in FIG. 10a, the flat abutment structure 570 abuts postero-laterally for a subject 200 with anteverted femora. Advantageously, the modified distal tip 550 sits in abutment in two locations providing more stable fixation than prior art prostheses. In contrast, the prior art distal end 170 has an elliptical or severely tapered cross-section that only provides a single-point of abutment 190b which is susceptible to sliding anteriorly and/or posteriorly across the lateral aspect of the endo-cortex 260. The inventive modified distal tip 550 with the flat abutment structure 570 substantially prevents anterior or posterior movement in the sagittal plane of the subject's femoral shaft 230 through two-point distal abutment fixation as shown.

Alternatively, the modified distal tip 550 may include a contoured abutment structure 580 as illustrated in FIGS. 9b and 10b. The contoured abutment structure 580 includes at least two contoured portions that each engage in abutment with the endo-cortex 260. FIG. 10b illustrates the cross-section of the contoured abutment structure 580 which generally has a figure-8 shape. As shown, the contoured abutment structure 580 sits in abutment with the endo-cortex 260, in a manner similar to the flat abutment structure 570, in order to provide abutment fixation with the endo-cortex 260 at two distal locations.

FIG. 9c illustrates another embodiment of the modified distal tip 550 which includes two rails 590 forming an abutment structure. The two rails each include flat engagement surfaces or edges, that respectively engage in abutment fixation with the lateral endo-cortex 260 at the two distal locations. This is illustrated with respect to FIG. 10c which shows a cross-sectional view of the two-rail abutment structure 590 within the subject's femoral shaft 230. The two-rail abutment structure 590 provides separation between the two rails 590 such that they engage at two locations on the endo-cortex 260. The rails engage postero-laterally to prevent movement of the modified distal tip 550 anteriorly and/or posteriorly in the sagittal plane of the subject's femoral shaft 230 during physiological loading.

Embodiments of the invention may provide a modular distal tip 550 which couples with an embodiment of the inventive prosthetic femoral implant 410 or pre-existing prior art prosthetic femoral stems 110 (not shown). Modularity gives a degree of flexibility in the hip prosthesis ultimately utilised and enables creation of a bespoke implant that has features selected or designed for a particular subject's anatomy. For example, the modified distal tip 550 may be available in various sizes or shapes such that the surgeon may select an appropriate distal tip 550 for accommodation and fixation in the subject's femoral shaft 230 and to better achieve taper-fit of the prosthesis in the subject's femoral neck 250.

In some embodiments, the two locations at which the modified distal tip 550 engages in abutment with the lateral endo-cortex 260 are aligned in a common transverse plane of the subject's femoral shaft 230, or with the remainder of the prosthesis. However, this need not be the case and in some cases, the distal two-point abutment fixation will occur, but may be not aligned in a common transverse plane.

3. Modified Distal Tip with Surface Contours to Improve Stability During Impaction In a preferred embodiment of the invention, an inventive femoral implant 410 includes the modified distal end 470 or tip 550 providing two-point abutment fixation at the lateral endo-cortex 260, and the contoured or recessed regions 520a and 520b providing re-distribution of net reaction forces along the elongate axis of the implant 410. An inventive femoral implant 410 including the modified distal end 470 and contoured regions 520a and 520b is shown in FIG. 5.

It is beneficial to provide both the modified distal end 470 and contoured regions 520a and 520b to improve stability of the femoral implant 410 during impaction, i.e. to reduce the induction of "spin". The distal tip modification providing two-point abutment fixation resists the torsional forces (described above) exerted on the prosthesis 410 at or near final impaction. This reduces the "spin" or torsional forces experienced by the femoral implant 410 within the femur 220, therefore reducing and more effectively resisting such forces. Overall, this provides improved stability of the femoral implant 410 reducing the likelihood of loosening and the risk of subsidence. Additionally, this combination of features comprising contours or recesses 520a, 520b and the modified distal tip 570 is intended to further stabilise the implanted prosthesis during early loading, i.e. before bone in-growth occurs.

4. Poor Anatomical Matching During Impaction

Instability of existing femoral stems 110 during impaction is also partly due to poor or non co-alignment of taper-fit fixation within the subject's femoral neck 250, as previously described, which may contribute to and more readily allow rotation around the elongate axis of the femoral stem 110. This is an issue particularly for anteverted femora as illustrated in FIG. 3 and retroverted femora (not shown), where the prosthetic femoral stem 110 is poorly aligned with the subject's femoral neck 250. FIG. 3 illustrates the poor endo-cortical taper-fit fixation occurring particularly on the anterior aspect of the femoral neck 250 due to non-concentric or non-aligned tapered surfaces of the prosthetic femoral stem 110.

Figure 12A:
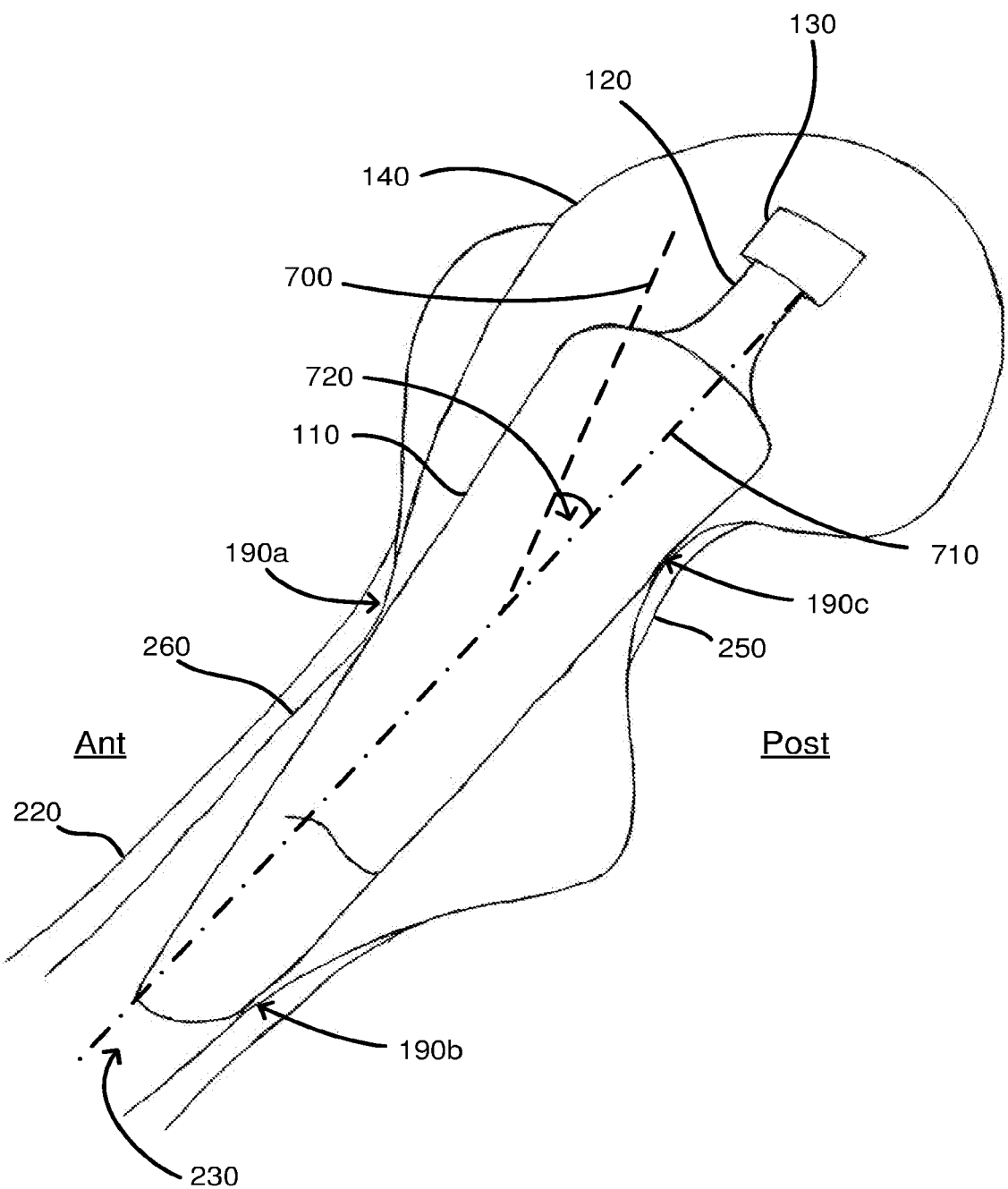
FIG. 12a illustrates a lateral view of the prior art prosthetic femoral stem of FIG. 1 implanted within a subject's left femur, which is normally anteverted, showing in broken lines, the axis of the proximal femur and the axis of the femoral neck of the femur, as well as the femoral head for illustrative purposes only.

The inventor has deduced that the main reason for the insufficient taper-fit fixation within the subject's femoral neck 250 is due to the non-curvature of the prosthetic femoral stem 110 with respect to the curvature of the femur 220 as shown in the lateral view, or the angle of anteversion of the femoral neck 250 with respect to the upper femoral shaft 230. This is illustrated in FIG. 12a, which shows a lateral view of the prosthetic femoral stem 110 implanted in a subject's anteverted femur 220. The femoral head 140 is also depicted for illustrative purposes only, since it is removed during hip arthroplasty. The prior art femoral stem 110, when viewed in the lateral view, is not curved to coincide with the angle 720 of the neck-shaft junction of the femur 220, as depicted in FIG. 12a, which is formed between two axes 700 and 710 of the femoral neck 250 and shaft 230, respectively. In contrast, the prior art femoral stem 110 appears to follow the femoral curvature as shown in the anterior-posterior or frontal view only, of FIG. 2, which is a more proximal and more gentle curvature than the angled curvature of the femur 220 shown in FIG. 12a.

The femoral prostheses of prior art neck-preserving and neck-fixed stems 110 are generally straight when viewed in the lateral view as shown in FIGS. 3 and 12a. These prostheses somewhat overlook the neck-shaft angle 720 and femoral curvature as shown in the lateral view of the femur 220 in FIG. 12a. Impaction of prior art femoral stems 110 therefore results in the prosthesis rotating into an anteverted position during impaction, such that the femoral stem 110 follows or conforms somewhat to both curves (as shown in the anterior-posterior and lateral views, respectively) of the femur 220. In order to address this, the inventive femoral implant 410 includes a second curve, to respect the neck-shaft angle 720 of the femur 220, so as to conform to both curves of the femur 220, better co-align the prosthesis 410 with the axis of the neck 250 and stabilise the prosthesis 410 against induced rotation during impaction.

Angled Distal Tip to Improve Alignment of Femoral Prosthesis

Embodiments of the inventive prosthetic femoral implant 410 include a distal end 470 angled in the sagittal plane of the subject's femur 220 to enable improved alignment with the subject's femoral curvature when implanted therein. The femoral implant 410 includes an angled distal tip 550 that incorporates an offset at an angle in the sagittal plane with respect to the elongate axis of the implant 410. The angled distal tip 550 is angled anteriorly in the sagittal plane of the subject's femur 220 when implanted therein. The angled distal tip 550 aims to correct the mis-match that occurs in anteverted femora to provide improved alignment and taper-fit of the implant 410 within the subject's femoral neck 250.

Figure 11A:
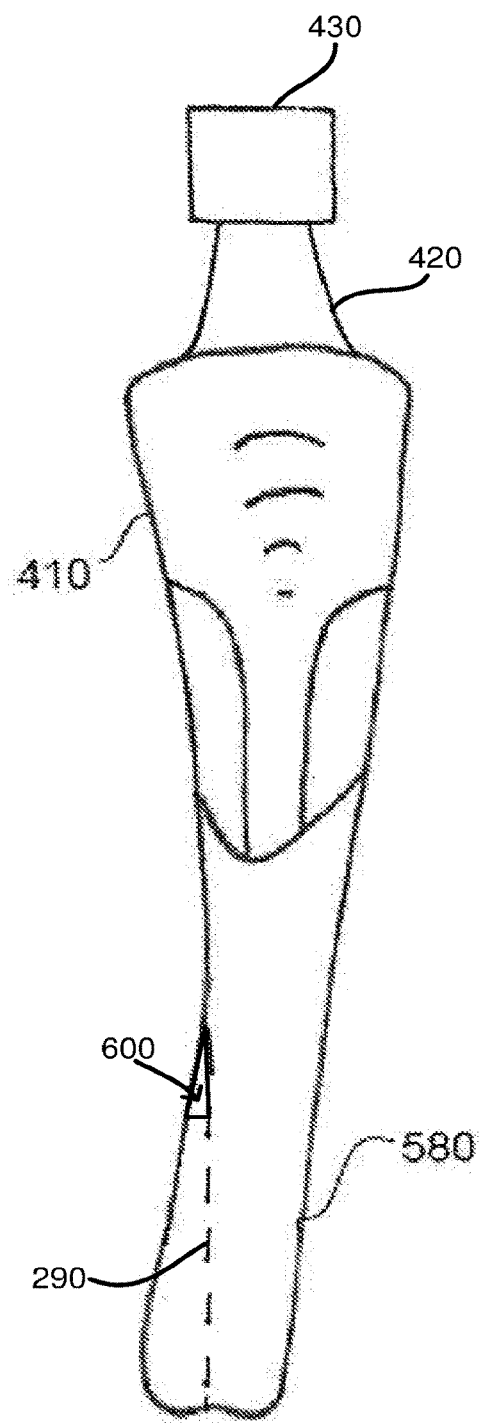
FIGS. 11a and 11b illustrate a lateral view of a femoral implant according to an embodiment of the invention, with a distal tip offset at an angle in the sagittal plane of the subject's left femur with respect to an elongate axis of the implant.
Figure 11B:
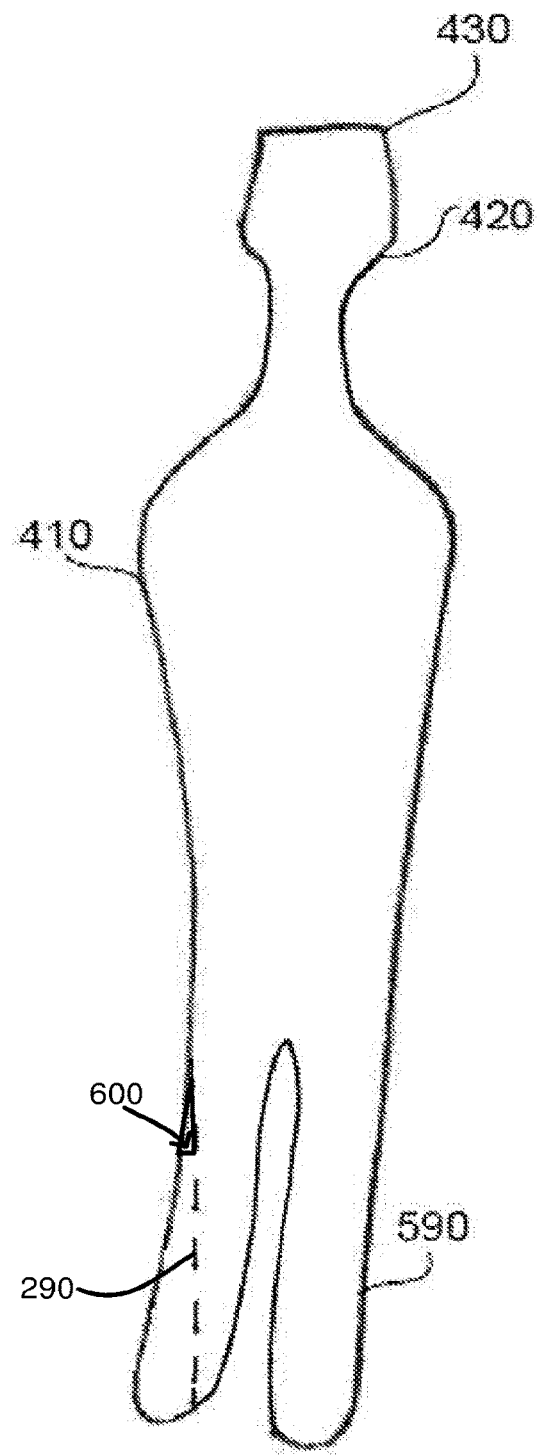
Figure 12B:
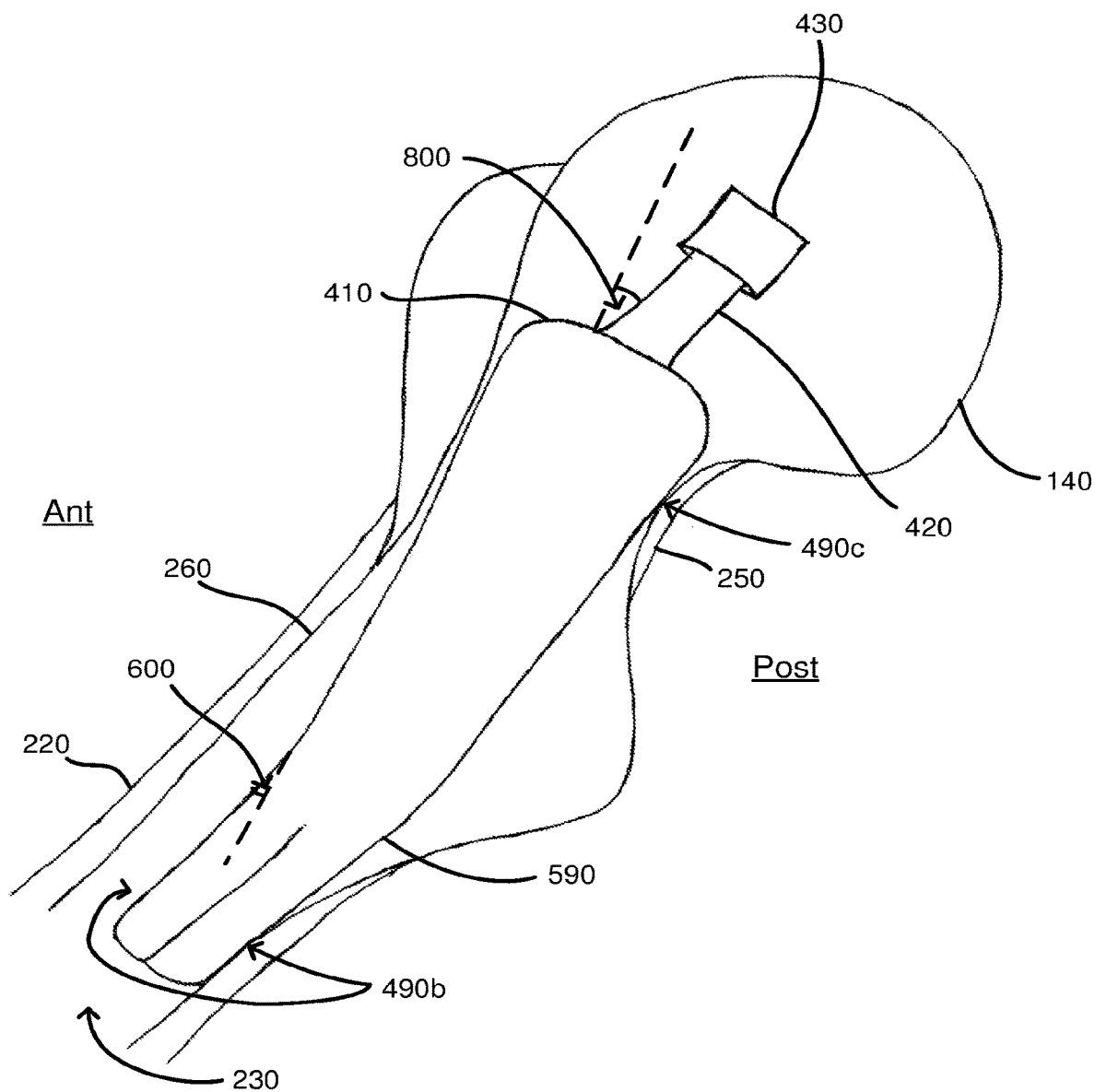
FIG. 12b illustrates a lateral view of the subject's left femur as shown in FIG. 12a with a femoral implant according to an embodiment of the invention implanted therein, having the angled distal tip of FIG. 11a and a neck portion offset at an angle in the sagittal plane of the subject's left femur and with respect to an elongate axis of the implant, showing improved alignment of the body of the prosthesis with the axis and the anterior endo-cortex of the subject's femoral neck.

FIGS. 11a and 11b illustrate embodiments of the inventive femoral implant 410 which include an offset angle 600 provided by an angled distal tip 550 having abutment structures 580 and 590, respectively, as shown in FIGS. 9b and 9c. These Figures show a lateral view of a left prosthetic femoral implant 410 in the anterior-posterior plane. Although the angled distal tips 550 include abutment structures 580, 590 in these embodiments, this need not be the case and the angled distal tips 550 may be tapered in a similar manner to prior art femoral stems 110 as described herein. The offset angle 600 is preferably in the range of about 5 to 25 degrees, more preferably about 10 to 20 degrees, and more preferably still, about 15 degrees. The offset angle 600 provides a more anatomically favourable shape for congruent implantation of the body of the prosthesis 410 within the subject's femoral neck 250 and respects the neck-shaft angle 720 of the subject's femur 220. This is illustrated in FIG. 12b, which shows a lateral view of the inventive femoral implant 410 of FIG. 11b implanted in the subject's anteverted femur 220. The distal tip 550 with abutment structure 590 as illustrated in FIG. 12b includes an offset angle 600 such that the femoral implant 410 better conforms to the angle 720 and endo-cortex 260 of the neck 250 of the subject's femur 220. This provides improved taper-fit fixation within the subject's femoral neck 250 thereby improving initial fixation of the implant 410. As co-alignment increases and taper fixation within the neck 250 is improved, PAP endo-cortical abutment fixation is thereby reduced, which therefore reduces induced "spin".

Angled Neck Portion to Improve Location of Head Centre of Femoral Prosthesis

Embodiments of the inventive prosthetic femoral implant 410 also include a neck portion 420 angled in a sagittal plane of the subject's femur to enable improved location of a femoral head of the implant 410 with respect to the subject's femoral neck 250 when implanted therein. The centre of the femoral head usually lies posterior to the axis of the femoral neck 250 for prior art femoral prostheses 110. In seeking to replicate a subject's normal "anterior drawer" or "anterior offset", the inventor has determined that it is desirable to angle the neck portion 420 posteriorly in the sagittal plane of the subject's femur 220.

As shown in FIG. 12b, the neck portion 420 is offset at an angle 800 in the sagittal plane with respect to the elongate axis of the implant 410, such that the neck portion 420 is angled posteriorly in the sagittal plane of the subject's femur 220 when implanted therein. The angled neck portion 420 is illustrated in FIG. 12b in conjunction with the angled distal tip 550. However, the angled neck portion 420 and angled distal tip 550 may be separately provided on the femoral implant 410. The offset angle 800 is preferably in a range of about 5 to 20 degrees, more preferably about 5 to 15 degrees, and more preferably still, about 10 degrees. As shown in FIG. 12b, the angled neck portion 420 achieves better conformity with the subject's anatomy through retro-tilting in the anterior-posterior or sagittal plane of the femur 220.

Angled Distal Tip and Neck Portion with Modified Distal Tip

The angled distal tips 550 shown in FIGS. 11a and 11b include abutment structures 580 and 590, respectively, as illustrated in FIGS. 9b and 9c. This provides improved distal abutment of the distal end 470 or the modified distal tip 550 with the endo-cortex 260 at the two distal locations further improving implant stability. It can be advantageous to provide an inventive femoral implant 410 with one or more of i) an angled distal tip and/or an angled neck portion to improve anatomical matching, and ii) a modified distal tip to improve distal fixation through two abutment points. For example, FIG. 12b illustrates the prosthetic femoral implant of FIG. 11b with the modified distal tip 590 providing two locations for abutment 490*b* distally of the prosthetic femoral implant 410. Furthermore, by combining this with the angled distal tip 550 and/or angled neck portion 420 it enables improved congruence with respect to the taper-fit fixation in the subject's femoral neck 250 as well as better replication of the subject's anatomy with respect to fore and aft location of the centre of the prosthetic femoral head ("anterior drawer" or "anterior offset"). These features when used separately or in combination provide improved stability at the distal end 470 both during impaction and also with physiological loading, as well as improved taper-fit fixation within the subject's femoral neck 250 and improved replication of normal anatomy.

5. Rotational Forces During Physiological Loading

In many cases, three-point abutment fixation (PAP for anteverted femora) of the prosthetic femoral stem 110, as previously described with reference to FIG. 3, is the main factor preventing movement of the prosthetic femoral stem 110 within the subject's femur 220 while bone in-growth occurs. This fixation may be insufficient to stabilise the prosthetic femoral stem 110 when the subject 200 is moving, such as when walking, or when the subject 200 is in the process of sitting or arising from the seated position.

The inventor has determined that before bone in-growth occurs, some prosthetic short femoral stems 110 are susceptible to cyclical micro-rotation around the elongate axis of the prosthesis 110, providing a lack of stability. FIG. 3 illustrates that the subject's normally anteverted femur, and that the prosthetic femoral stem 110 is commonly stabilised through three-point abutment fixation with the endo-cortex 260, as previously described. However, when the subject 200 is seated or walking, the forces applied due to physiological loading are such that the reaction forces at the three abutment points 190*a*, 190*b* and 190*c* are no longer balanced, i.e. they are directly opposed or reduced by the forces applied due to physiological loading.

Femora that are anteverted or retroverted are fixed in posterior-anterior-posterior (PAP) or anterior-posterior-anterior (APA) abutment, respectively. As a result, there are forces applied at a normal or directly through the transverse plane of the prosthetic femoral stem 110. Since the prosthetic femoral stem 110 typically has a curved elongate axis, the three-point loading for femoral stems 110 implanted in anteverted or retroverted femora can be characterised as loading of a curved "beam". Unlike three-point loading of a straight "beam", three-point loading of a curved "beam" at a normal to that curve is inherently unstable, as it induces a rotational force around the elongate axis.

In addition, depending on the subject's orientation, loading of the subject's femur 220 such as in attempting to sit or arise from sitting, can cause rotation of the prosthetic femoral stem 110 around its elongate axis, i.e. within the subject's femur 220, resulting in failure of primary stability. Ultimately, this can cause early loosening and subsidence of the prosthetic femoral stem 110 within the subject's femur 220.

Surface Contours to Reduce Rotational Forces

As previously described, a preferred embodiment of the inventive prosthetic femoral implant 410 includes a contoured surface to redistribute the net reaction forces in each transverse plane along the elongate axis of the implant 410. Contoured or recessed regions 520*a* and 520*b* effectively shift the location of the net reaction forces in the anterior-posterior direction of the transverse plane. The effect of this is that the curved "beam" becomes somewhat "straighter" (see FIG. 7). Advantageously, a straighter "beam" provides greater stability under three-point loading in a subject 200 with anteverted or retroverted femora, by reducing the curvature upon which the 3-point fixation is applied. Accordingly, not only does providing a contoured surface reduce torsional forces during impaction, it also reduces induction of rotational forces during physiological loading such as standing which mimics the direction of impaction forces, by providing a straighter "beam" for 3-point loading, without altering the general curvature of the implant 410.

Modified Distal Tip with Surface Contours to Reduce Rotational Forces

Additionally, a femoral implant 410 with the modified distal tip 550 and contoured or recessed surfaces 520*a*, 520*b* reduce rotational forces during physiological loading. The modified distal tip 550 or distal end 470 is stabilised in the coronal and sagittal planes of the subject's femoral shaft 230, which prevents sliding fore and aft across the lateral endo-cortex 260. The two-point abutment fixation resists the cyclical micro-rotation around the elongate axis of the femoral implant 410, which may occur during early physiological loading.

6. Limited Extent of Porous Coating

As described above, prior art prosthetic femoral stems 110 include a porous coating to encourage bone in-growth during post-surgical recovery. The coating plays an essential role in facilitating bone in-growth to the extent that the short-stem hip prosthesis 100 may be stabilised in the subject 200 after it is implanted. Once in-growth occurs, the porous surface is responsible for stress or load transfer between the prosthesis 110 and the subject's femur 220, i.e. all loads across the hip. However, current femoral stems 110 include an extensive coating, circumferentially at the proximal end 180, such that the bone in-growth toward the distal end of said coating ultimately produces stress shielding of more proximal bone. Furthermore, proximal bone in-growth obstructs ready access to the more distal portion of in-grown bone for the purpose of revision surgery. As a result, with prior art designs, the cortical bone of the subject's femur 220 may be damaged during removal from the in-grown bone necessary for removal of the prosthetic femoral stem 110.

Thus, another aspect of the invention provides a femoral implant 410 with a coating 560 comprising a bone in-growth promoting substance that is positioned to overcome or at least ameliorate two of the problems with the prior art, i.e. stress shielding of proximal bone and poor access to the more distal portion of in-grown bone for revision surgery. In one embodiment, the coating of bone in-growth promoting substance is applied to the prosthetic femoral implant 410 medially from below the neck portion 420 to about one-third of the implant length and laterally to about one-half to two-thirds of the length of the implant 410. Limiting the extent of the coating in this way can reduce the likelihood of damage to a subject's femur during revision surgery.

Figure 13:
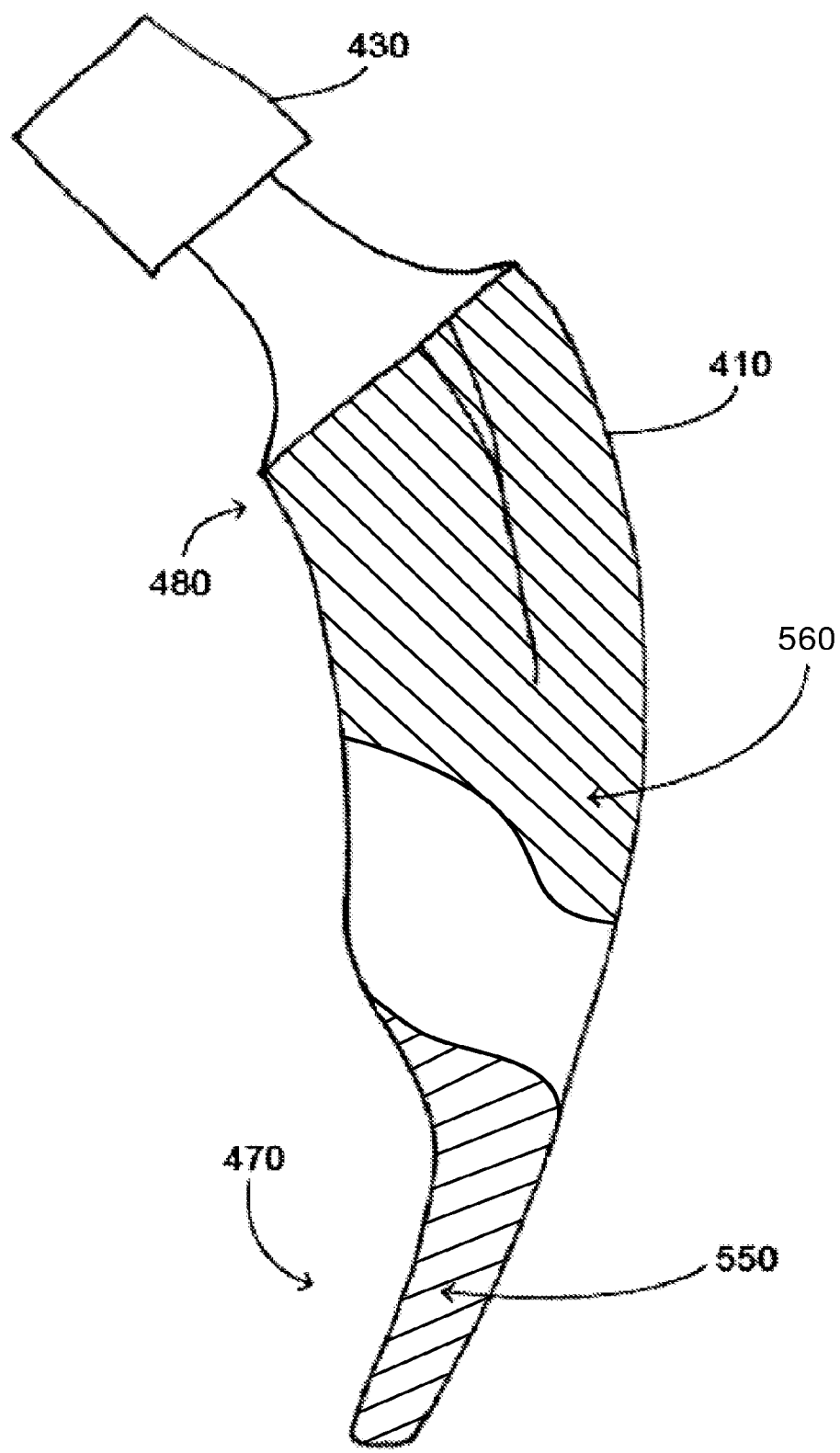
FIG. 13 illustrates a frontal view of a femoral implant according to an embodiment of the invention, showing a bone in-growth coating in a modified format that allows for relative ease of removal for revision surgery if necessary, and additionally, the modified distal tip of FIG. 8.
Figure 14:
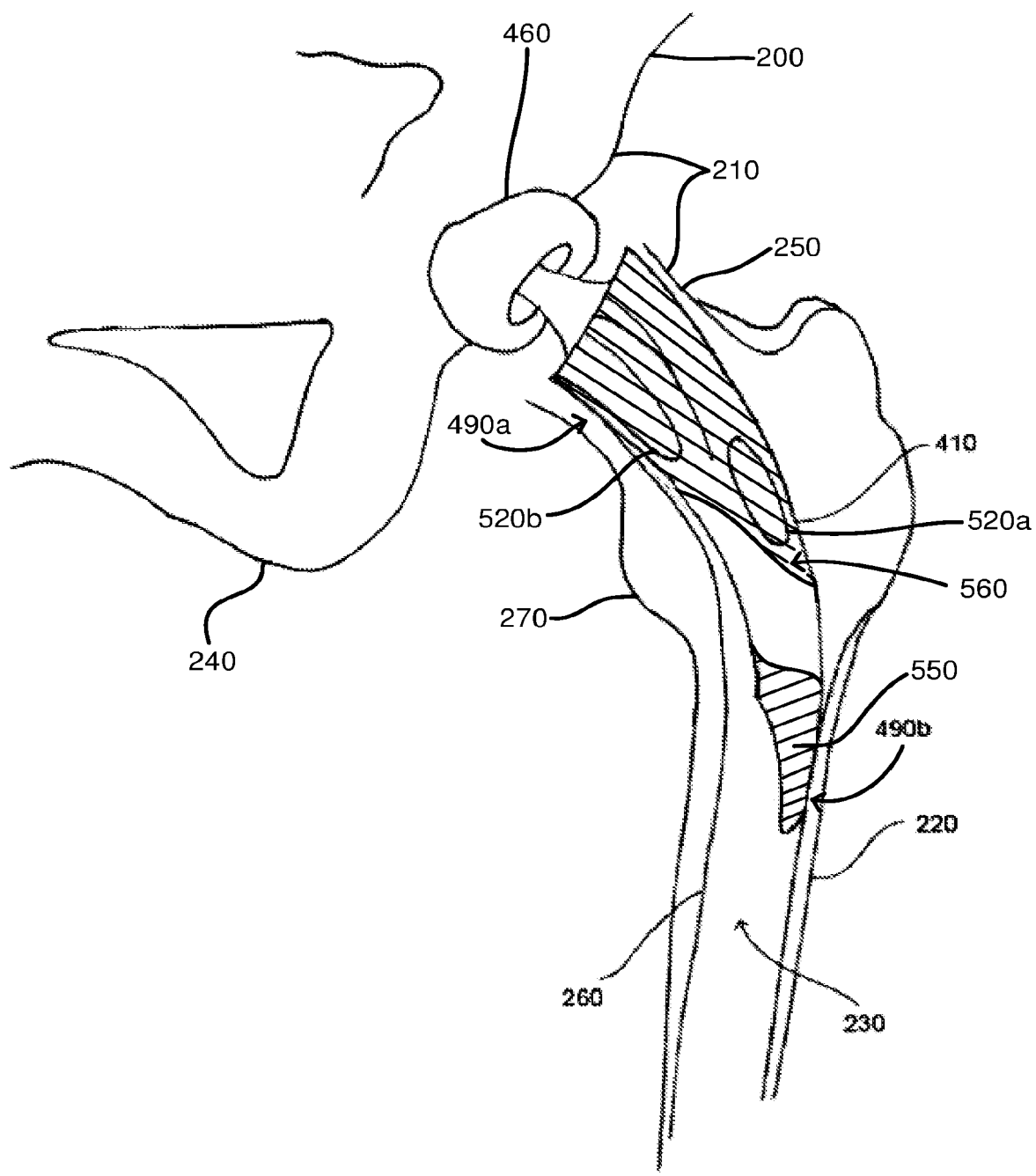
FIG. 14 illustrates a frontal view of a hip prosthesis according to an embodiment of the invention, implanted within a subject's left femur, when the subject is stationery and standing. The hip prosthesis includes the features of the recessed regions shown in FIG. 5 and the modified distal tip and bone in-growth coating shown in FIG. 13.

FIGS. 13 and 14 illustrate the inventive porous coating 560 positioned on a prosthetic femoral implant 410. FIG. 14 also shows the contoured or recessed regions 520*a* and 520*b* which in addition to re-shaping the surface of the femoral implant 410 to re-distribute net reaction forces, produces 'flattened' facets of porous coated surface, which are accessible for a surgeon to dissect from above, with reduced damage to the surrounding femur, during revision surgery, should it be required. The prosthetic femoral implant 410 may be provided only with the restricted porous coating 560 or be provided in combination with the flattened portions 520*a* and 520*b*, since removal of in-grown bone from the proximal implant surface only, can be more straightforward.

Preferably, the bone in-growth substance used in the coating is calcium hydroxy-apatite, calcium apatite, or other bone in-growth inductive or conductive material known to a person skilled in the art. The coating may be applied to the prosthetic femoral implant 410 through suitable processes such as plasma spraying, which is in turn applied to a scinted or porous coating of pure titanium or other porous material known to a person skilled in the art.

7. Combined Features for Improved Stability During Impaction and Physiological Loading While various aspects of the invention are described separately in the context of certain embodiments, it is to be understood that an inventive hip prosthesis 400 or an inventive femoral implant 410 for use in hip arthroplasty may include any one or more of the features disclosed herein in any combination, and drawn from any of the aspects of the invention and the embodiments herein described. Thus, it is to be understood that each of the inventive features may be utilised separately or in any combination to address undesired forces of rotation, translation and/or torsion that can otherwise lead to implant instability, loosening, subsidence and failure known to occur with existing short-stem hip prostheses. The femoral implant 410 shown in FIG. 14 illustrates an embodiment in which all aspects of the invention are present.

FIG. 14 illustrates a frontal view of an inventive hip prosthesis 400 implanted within a subject's left femur 220. The hip prosthesis 400 includes the inventive femoral implant 410 shown in FIG. 14, incorporating 1) the contoured or recessed regions 520a, 520b, 2) the modified distal end 470 with distal tip 550, 3) the anatomically angled tip and/or neck portion (although not visible in this view), and 4) the inventive limited extent of proximal coating 560. The inventive hip prosthesis 400 includes a femoral head 440 positioned on the prosthetic femoral implant 410 (not clearly shown). Furthermore, the inventive hip prosthesis 400 includes an acetabular liner 450 (not shown) and an acetabular cup 460 which are positioned to accommodate the femoral head 440. Two-point abutment fixation of the inventive hip prosthesis 400 is illustrated in FIG. 14 through abutment points 490a and 490b, which are similarly positioned with respect to the prior art hip prosthesis 100 shown in FIG. 2. However, two-point distal fixation at 490b is present due to the modified distal tip 550 but is not visible in this view.

8. Reduced Offset Angle

Furthermore, a preferred embodiment of the inventive prosthetic femoral implant 410 includes a reduced offset angle between the neck 420 of the prosthesis and the elongate axis of the prosthetic femoral implant 410 (not shown). Providing a reduced offset angle is desirable in order to reduce torsional forces exerted at the bone-implant interface. The torsional force is dependent at least in part on the offset angle and the subject's weight. By providing a reduced offset angle, the torsional force on the prosthetic femoral implant 410 will be reduced, thereby significantly reducing rotational forces around the elongate axis of the prosthetic femoral implant 410. This in turn reduces the likelihood of loosening and subsidence of the prosthetic femoral implant 410 within the subject's femur 220. Ideally, the offset angle is less than about 40 degrees. It is also preferable to include a 12/14 inch tapered trunion 430.

It is to be understood that various modifications, additions and/or alterations may be made to the parts previously described without departing from the ambit of the present invention as defined in the claims appended hereto.

It is to be understood that the following claims are provided by way of example only, and are not intended to limit the scope of what may be claimed in any future application. Features may be added to or omitted from the claims at a later date so as to further define or re-define the invention or inventions.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereto.

The invention claimed is:

1. A short-stem femoral implant suitable for use in hip arthroplasty, the femoral implant including a neck portion angled in a sagittal plane of the subject's femur to enable improved location of a femoral head of the implant with respect to the subject's femoral neck when implanted therein, wherein the neck portion is angled posteriorly with respect to an elongate axis of the femoral implant.

2. The femoral implant according to claim 1, wherein the neck portion is offset at an angle in a range of about 5 to 15 degrees in the sagittal plane.

3. The femoral implant according to claim 1, further including a distal end angled in a sagittal plane of the subject's femur to enable improved alignment with the subject's femoral curvature when implanted therein.

4. The femoral implant according to claim 3, wherein the distal end is offset at an angle in a range of about 10 to 20 degrees in the sagittal plane.

5. The femoral implant according to claim 3, wherein the distal end is angled anteriorly with respect to an elongate axis of the femoral implant.

6. The femoral implant according to claim 1, further configured to preserve at least some of the subject's femoral neck when implanted therein.

7. The femoral implant according to claim 1, further configured for ease of removal from the subject's femur by including a bone in-growth coating suitably positioned for revision surgery, wherein the coating is positioned proximally about one-third medially and about one-half to two-thirds laterally so as to not obscure access to the femoral bone-implant interface distally during removal from the subject's femur.

8. The femoral implant according to claim 1, further configured to self-stabilize against rotation about an elongate axis thereof when implanted in a subject's femur, wherein the femoral implant includes a contoured surface having one or more recessed regions configured to distribute reaction forces imparted at the bone-implant interface such that when implanted, the femoral implant has a reduced tendency to rotate about the elongate axis.

9. The femoral implant according to claim 1, further configured to self-stabilise against sliding across the endo-cortex when implanted in the subject's femur, wherein the femoral implant includes a distal end configured to engage in abutment with the lateral endo-cortex of the subject's femur at two distal locations such that when implanted, the femoral implant has a reduced tendency for sliding across the endo-cortex.

10. A short-stem femoral implant suitable for use in hip arthroplasty, the femoral implant including a neck portion angled in a sagittal plane of the subject's femur to enable improved location of a femoral head of the implant with respect to the subject's femoral neck when implanted therein, further including a distal end angled in a sagittal plane of the subject's femur to enable improved alignment with the subject's femoral curvature when implanted therein, wherein the distal end is angled anteriorly with respect to an elongate axis of the femoral implant.

11. A short-stem femoral implant suitable for use in hip arthroplasty, the femoral implant including a neck portion angled in a sagittal plane of the subject's femur to enable improved location of a femoral head of the implant with respect to the subject's femoral neck when implanted therein, further configured for ease of removal from the subject's femur by including a bone in-growth coating suitably positioned for revision surgery, wherein the coating is positioned proximally about one-third medially and about one-half to two-thirds laterally so as to not obscure access to the femoral bone-implant interface distally during removal from the subject's femur.

12. The femoral implant according to claim 11, wherein the distal end is angled anteriorly with respect to an elongate axis of the femoral implant.

13. The femoral implant according to claim 12, wherein the distal end is offset at an angle in a range of about 10 to 20 degrees in the sagittal plane.

14. The femoral implant according to claim 11, further configured to self-stabilize against rotation about an elongate axis thereof when implanted in a subject's femur, wherein the femoral implant includes a contoured surface having one or more recessed regions configured to distribute reaction forces imparted at the bone-implant interface such that when implanted, the femoral implant has a reduced tendency to rotate about the elongate axis.

15. The femoral implant according to claim 11, further configured to self-stabilise against sliding across the endo-cortex when implanted in the subject's femur, wherein the femoral implant includes a distal end configured to engage in abutment with the lateral endo-cortex of the subject's femur at two distal locations such that when implanted, the femoral implant has a reduced tendency for sliding across the endo-cortex.

16. The femoral implant according to claim 11, wherein the neck portion is angled posteriorly with respect to an elongate axis of the femoral implant and is offset at an angle in a range of about 5 to 15 degrees in the sagittal plane.

17. The femoral implant according to claim 11, wherein the neck portion is angled posteriorly with respect to an elongate axis of the femoral implant and is offset at an angle in a range of about 5 to 15 degrees in the sagittal plane.

18. A short-stem femoral implant suitable for use in hip arthroplasty, the femoral implant including a neck portion angled in a sagittal plane of the subject's femur to enable improved location of a femoral head of the implant with respect to the subject's femoral neck when implanted therein, further configured to self-stabilize against rotation about an elongate axis thereof when implanted in a subject's femur, wherein the femoral implant includes a contoured surface having one or more recessed regions configured to distribute reaction forces imparted at the bone-implant interface such that when implanted, the femoral implant has a reduced tendency to rotate about the elongate axis.

19. The femoral implant according to claim 18, wherein the one or more recessed regions are positioned on the femoral implant such that the reaction forces are transferred medially and/or laterally in a transverse plane of the subject's femur.

20. The femoral implant according to claim 19, wherein the one or more recessed regions are positioned near or at a location where the femoral implant engages in abutment with the endo-cortex of the subject's femur, and wherein two or more recessed regions are included on one or both of an anterior aspect and a posterior aspect of the femoral implant.

21. The femoral implant according to claim 18, wherein the recessed regions are formed in the contoured surface as one of: a bevel; a hollow; a flattened edge; a sloped edge; or a chamfer.

22. A short-stem femoral implant suitable for use in hip arthroplasty, the femoral implant including a neck portion angled in a sagittal plane of the subject's femur to enable improved location of a femoral head of the implant with respect to the subject's femoral neck when implanted therein, further configured to self-stabilise against sliding across the endo-cortex when implanted in the subject's femur, wherein the femoral implant includes a distal end configured to engage in abutment with the lateral endo-cortex of the subject's femur at two distal locations such that when implanted, the femoral implant has a reduced tendency for sliding across the endo-cortex.

23. The femoral implant according to claim 22, wherein the distal end includes one of:
    a flat abutment structure configured to engage in abutment with the lateral endo-cortex at the two distal locations;
    a contoured abutment structure configured to engage in abutment with the lateral endo-cortex at the two distal locations; or
    two rails forming an abutment structure, wherein the two rails each include flat engagement surfaces or edges that respectively engage in abutment with the lateral endo-cortex at the two distal locations.

24. The femoral implant according to claim 22, further configured to self-stabilize against rotation about an elongate axis thereof when implanted in a subject's femur, wherein the femoral implant includes a contoured surface having one or more recessed regions configured to distribute reaction forces imparted at the bone-implant interface such that when implanted, the femoral implant has a reduced tendency to rotate about the elongate axis.

* * * * *